(12) United States Patent
Sichtnik

(10) Patent No.: US 10,183,964 B2
(45) Date of Patent: Jan. 22, 2019

(54) COMPOSITIONS AND METHODS FOR TREATING INFECTIOUS DISEASE

(71) Applicant: Laszlo Sichtnik, Bronx, NY (US)

(72) Inventor: Laszlo Sichtnik, Bronx, NY (US)

(73) Assignee: Laszlo Sichtnik, Bronx, NY (US)

( * ) Notice: Subject to any disclaimer, the term of this patent is extended or adjusted under 35 U.S.C. 154(b) by 14 days.

(21) Appl. No.: 14/851,100

(22) Filed: Sep. 11, 2015

(65) Prior Publication Data

US 2016/0002277 A1 Jan. 7, 2016

Related U.S. Application Data

(63) Continuation-in-part of application No. PCT/US2014/024262, filed on Mar. 12, 2014.

(60) Provisional application No. 61/777,484, filed on Mar. 12, 2013.

(51) Int. Cl.
  *C07H 15/18* (2006.01)
  *A61K 31/7028* (2006.01)
  *A61K 31/704* (2006.01)

(52) U.S. Cl.
  CPC .......... *C07H 15/18* (2013.01); *A61K 31/704* (2013.01); *A61K 31/7028* (2013.01)

(58) Field of Classification Search
  CPC ... A61K 31/704; A61K 31/7028; C07H 15/18

USPC ........................................... 514/25; 536/17.9
See application file for complete search history.

(56) References Cited

U.S. PATENT DOCUMENTS

| | | | |
|---|---|---|---|
| 2006/0257508 A1* | 11/2006 | Khayat | A61K 31/7034 424/735 |
| 2008/0261291 A1 | 10/2008 | Romero | |
| 2011/0008467 A1 | 1/2011 | Sherman et al. | |

FOREIGN PATENT DOCUMENTS

| | | | |
|---|---|---|---|
| CN | 102702282 | | 10/2012 |
| EP | 0023178 | | 1/1981 |
| GB | 788855 | * | 1/1958 |
| JP | 2003113088 | | 4/2003 |

OTHER PUBLICATIONS

Hall et al, Annals of Emergency Medicine, 2007, 49(6), 808-813.*
Al-Bakri et al., "Antibacterial Activity of Apricot Kernel Extract Containing Amygdalin," *Iraq J. Sci.* 51(4):571-576, 2010.

* cited by examiner

*Primary Examiner* — Ganapathy Krishnan
(74) *Attorney, Agent, or Firm* — Occhiuti & Rohlicek LLP

(57) ABSTRACT

Provided are cyanogenic compositions for treating diseases, such as infectious diseases.

14 Claims, No Drawings

COMPOSITIONS AND METHODS FOR TREATING INFECTIOUS DISEASE

CROSS-REFERENCE TO RELATED APPLICATIONS

This application claims priority to PCT/US2014/024262, filed Mar. 12, 2014 and U.S. Ser. No. 61/777,484, filed Mar. 12, 2013. The contents of these applications are incorporated herein by reference in their entireties.

BACKGROUND

Certain plants, such as members of the Sapindaceae family and edible plants like sorghum and lima beans, contain cyanogenic secondary metabolites. Plants store their cyanogenic secondary metabolites in compartments separated from catabolic or hydrolyzing enzymes. The breakdown of the cyanogenic secondary metabolites and subsequent cyanide (CN—) liberation does not occur until damage to the plant causes mixing of the enzyme and substrate components. Cyanogenic secondary metabolites are stable in the absence of a catabolic enzyme.

SUMMARY

The invention is based in part on the discovery that cyanogenic glycosides and their chemically active groups—cyanohydrins—are safe and effective against infectious disease when administered to animals, including humans. A large amount of stabilized cyanogenic compound can be ingested by or injected into an animal or human body without toxic side effects, although compositions according to the invention are effective at low dosage.

The compositions and methods provide a broad spectrum medication that has an enormous advantage in health care and epidemiology of humans and animals, including areas of the world where specific diagnostic testing is not readily available. Efforts to eradicate infectious diseases can benefit immensely from rapidly eliminating the infective virus from the patients, thereby reducing spreading the virus. The compositions and methods disclosed herein can also be used to prevent the spreading of diseases to susceptible people or animals.

Suitable compositions useful in the invention include cyanogenic glycosides and/or their synthetic versions and derivatives, cyanohydrins and their salts and their conjugates and derivatives and other groups, and cyanolipids (Types I-IV) and their derivatives. The compositions are effective against virus, bacteria, fungus, parasites and protozoa. Accordingly, the compositions are capable of preventing and curing viral, bacterial, fungal, parasitic and protozoa induced disease. They are additionally useful for treating inflammation, including inflammation associated with disease. Inflammation can be acute or chronic.

In one aspect, the invention provides a method of treating an infectious disease comprising administering a pharmaceutically effective amount of one or more cyanogenic compounds or a pharmaceutically acceptable salt, a solvate, or a hydrate thereof, to a patient in need thereof. The one or more cyanogenic compounds can each independently include one or more cyanogenic glycosides, one or more cyanohydrins, one or more cyanolipids, or a combination thereof.

In some embodiments, the glycoside can include a monosaccharide, or an oligosaccharide comprising two or more monosaccharides. The monosaccharide can be a pentose or a hexose, and can be acyclic or cyclic. For examples, the monosaccharide can be a rhamnose, arabinose, mannose, glucose, or xylose.

In some embodiments, the one or more cyanogenic glycosides each independently comprise acalyphin, acacipetalin, amygdalin, anaglyphic, cardiospermin, deidaclin, dihydromaronin, dhurrin, epidermin, epilucumin, epiproacacipetalin, epiheterodendrin, epilotaustralin, epivolkenin, grayanin, gynocardin, heterodendrine, holocalin, isosarmentosin, isotriglochinin, linamarin, linustatin, lotaustralin, lucumin, nandinin, neolinustatin, oxyanthin, benzoate oxyanthin, passicapsin, passibiflorin, passitrifasciatin, proacacipetalin, proacaciberin, proteacin, prunasin, sambunigrin, samentosin, suberin, sutherlandin, taraktophyllin, taxiphyllin, tetraphyllin, triglochinin, vicianin, volkenin, xeranthin, zierin, zierinxyloside, or a combination thereof.

In some embodiments, the one or more cyanohydrins are each independently acetone cyanohydrin, acetaldehyde cyanohydrin, cyanohydrin, butyraldehyde cyanohydrin, methyl ethyl ketone cyanohydrin, methyl isopropyl ketone cyanohydrin, methyl t-butyl ketone cyanohydrin, cyclobutanone cyanohydrin, cyclopentanone cyanohydrin, cyclohexanone cyanohydrin, benzaldehyde, cyanohydrin, p-methoxybenzaldehyde cyanohydrin, o-methoxybenzaldehyde, cyanohydrin, diethylketone cyanohydrin, methylbutylketone cyanohydrin, cyclododecanone cyanohydrin, propionaldehyde cyanohydrin, and furfuraldehyde, or cyanohydrin, or a combination thereof.

In some embodiments, the one or more cyanolipids each independently comprise one or more Class I cyanolipids, one or more Class II cyanolipids, one or more Class III cyanolipids, one or more Class IV cyanolipids, or a combination thereof.

In some embodiments, the one or more cyanolipids each independently comprise L-leucine.

In some embodiments, the infectious disease is caused by one or more bacteria, one or more viruses, one or more protozoa, one or more fungi, or one or more parasites, or a combination thereof.

In some embodiments, the one or more bacteria each independently include one or more pathogenic bacteria.

In some embodiments, the one or more bacteria each independently include *Bacillus, Bartonella, Bacterioides, Bordetella, Borrelia, Brucella, Campylobacter, Chlamydia, Chlamydophila, Clostridium, Corynebacterium, Coxiella, Enterococcus, Escherichia, Ehrilichia, Francisella, Fusobacterium, Haemophilus, Helicobacter, Legionella, Leptospira, Listeria, Mycobacterium, Mycoplasma, Moraxella, Neisseria, Pasteurella, Pseudomonas, Rickettsia, Rochalimaea, Salmonella, Shigella, Staphylococcus, Streptococcus, Treponema, Vibrio, Yersinia*, or a combination thereof.

In some embodiments, the one or more bacteria are each independently one or more antibiotic resistant bacteria. For example, the one or more antibiotic resistant bacteria can each independently include Methicillin-resistant *Staphylococcus aureus*, vancomycin resistant *Enterococcus*, multidrug-resistant *Mycobacterium tuberculosis*, or a combination thereof.

In some embodiments, the one or more viruses each independently include one or more pathogenic RNA viruses, one or more pathogenic DNA viruses, or a combination thereof.

In some embodiments, the one or more viruses each independently include Adenoviridae, Papillomaviridae, Parvovirdea, Herpesviridae, Poxviridae, Hepadnaviridae, Polyomaviridae, Anelloviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, Hepeviridae, Hepatitis B virus, Asfarviridae, or a combination thereof.

In some embodiments, the one or more protozoa each independently include *Acineta, Actinophrys, Actinosphaerium, Amphidinium, Amphileptus, Amphisiella, Anisonema, Anthophysis, Arcella, Blepharisma, Calocyclas, Carchesium, Centropyxis, Chilodonella, Chilomonas, Colpes, Colpoda, Cyclidium, Dictyoprora, Difflugia, Dileptus, Diophrys, Disematostoma, Diplomonada, Epistylis, Euglena, Euglypha, Euplotes, Eusyringium, Frontonia, Halteria, Heliodiscus, Heteronema, Hexastylus, Ichthyophthirius, Keronopis, Lacrymaria, Leishmania, Lembadion, Lithochytris, Litonotus, Lophospyris, Loxophyllum, Nassula, Opalina, Ophrydium, Oxytricha, Paramecium, Peranema, Peridinium, Phacus, Plasmodium, Pleuronema, Podocyrtis, Pyxicola, Rhabdostyla, Rhizamoeba, Spiroloculina, Spirostomum, Stichotricha, Strombidium, Stylonychia, Tetrahymena, Thuricola, Thyrsocyrtis, Trachelomonas, Tracheloraphis Trichomonas, Trypanosoma, Urocentrum, Urostyla, Vorticella, Xiphosphaera, Xiphostylus*, or a combination thereof.

In some embodiments, the one or more fungi each independently include *Alternaria, Aspergillus, Blastomyces, Candida, Ceratocystis, Chrysosporium, Coccidiodes, Cryptococcus, Epidermophyton, Exophiala, Fusarium, Helminthsporium, Histoplasma, Microsporum, Paracoccidioides, Penicillium, Paecilomyces, Pityrosporum, Saccharomyces, Sporothrix, Trichophyton*, or a combination thereof.

In some embodiments, the one or more parasites each independently include one or more parasitic roundworms, one or more parasitic flatworms, or a combination thereof.

In some embodiments, the one or more parasitic roundworms include *Ascaris*. In some embodiments, the parasitic flatworms include *Schistosoma*.

In some embodiments, the one or more cyanogenic compounds have a high bioavailability.

In some embodiments, the one or more cyanogenic compounds are each independently formulated as water-soluble or lipid soluble salts or conjugates. In some embodiments, the one or more cyanogenic compounds each independently include one or more pharmaceutically acceptable purified plant extracts.

In some embodiments, one or more antiviral medicines, one or more antibiotics, one or more antiparasitic medicines, one or more anti-malaria medicines, one or more antifungal medicines, or a combination thereof, are administered with the cyanogenic composition.

In some embodiments, one or more antiviral medicines each independently include acyclovir, famciclovir, valaciclovir, amantadine, oseltamivir, rimantidine, zanamivir, cidofovir, foscarnet, ganciclovir, ribavirin, penciclovir, buciclovir, acyclic guanosine derivatives, (E)-5-(2-bromovinyl)-2'-deoxyuridine, bacavir, didanosine, emtricitabine, lamivudine, stavudine, tenofovir, zalcitabine, zidovudine, delavirdine, efavirenz, etravirine, nevirapine, amprenavir, atazanavir, darunavir, fosamprenavir, indinavir, lopinavir/ritonavir, nelfinavir, ritonavir, saquinavir, tipranavir, enfuvirtide, maraviroc, raltegravir, or a combination thereof.

In some embodiments, the one or more antibiotics each independently include cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, or a combination thereof.

In some embodiments, the one or more antiparasitic medicines each include, independently, albendazole, amphotericin B, diethylcarbamazine, eflornithine, ivermectin, mebendazole, melarsporal, metronidazole, miltefosine, niclosamide, praziquantel, pyrantel pamoate, rifampin thiabendasole, tinidazole, yinidazole, or a combination thereof.

In some embodiments, the one or more anti-malaria medicines each independently include amodiaquine, artemether, artemisinin, atovaquone-proguanil, coartem, hydroxychloroquine, lumefantrine, or a combination thereof.

In some embodiments, the one or more antifungal medicines each include, independently, Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, ciclopirox olamine, Flucytosine, Griseofulvin, Haloprogin, Polygodial, Tolnaftate, Undecylenic acid, crystal violet, or a combination thereof.

In some embodiments, dimethyl sulfoxide is co-administered with the cyanogenic compound.

In some embodiments, the cyanogenic compound is administered with one or more biofilm destroying agents. The one or more biofilm destroying agents can, e.g., each independently include a combination of one or more 2-aminoimidazoles with one or more antibiotics, clarithromycin, iodine, one or more essential oils, Serrapeptase, or a combination thereof.

In some embodiments, the one or more essential oils each independently include Rosemary, peppermint, tea tree, garlic, aloe vera, licorice, St. John's wort, clove, thyme, cranberry, green tea, buchu, rooibus, echinacea, spearmint, eucalyptus, Ginger grass, clove oil, or a combination thereof.

In some embodiments the cyanogenic compound is administered with sodium thiosulfate, potassium thiosulfate, or a combination thereof.

In some embodiments, the one or more cyanogenic compounds are each independently formulated in a pill, a capsule, a granule, a tablet, a pallet, a suspension, an injection, an infusion, a suppository, a continuous delivery system, a syrup, a tincture, an ointment, a cream, an eye drop, an eardrop, a flush, a lavage, a slow absorbing depot, a dressing, or a lozenge.

In some embodiments, the one or more cyanogenic compounds are each independently administered intravenously, intramuscularly, subcutaneously, intraperitonialy, intrapleuraly, intrabrochialy, intrauterine, orally, topically, rectally, into joints, into the urinary system, into bone and teeth, into a gingival pocket, into an ear, into an eye, into conjunctiva, into the nose and sinuses, sublingually, intrathecally, intraarthicularly, or into cerebrospinal fluid.

In some embodiments, the one or more cyanogenic compounds are applied as a wound dressing.

In some embodiments, the patient is a mammal e.g., a domesticated animal such as a dog or cat. In other embodiments, the patient is a human.

In another aspect, the invention provides a method of treating an infectious disease by administering a pharmaceutically effective amount of amygdalin, a solvate, or a hydrate thereof, to a mammal in need thereof.

In some embodiments, the infectious disease is from one or more bacteria, one or more viruses, one or more protozoa, one or more fungi, one or more parasites, or a combination thereof.

In some embodiments, the one or more bacteria each independently include one or more pathogenic bacteria.

In some embodiments, the one or more bacteria each independently include *Bacillus, Bartonella, Bacterioides, Bordetella, Borrelia, Brucella, Campylobacter, Chlamydia, Chlamydophila, Clostridium, Corynebacterium, Coxiella, Enterococcus, Escherichia, Ehrlichia, Francisella, Fusobacterium, Haemophilus, Helicobacter, Legionella, Leptospira, Listeria, Mycobacterium, Mycoplasma, Moraxella, Neisseria, Pasteurella, Pseudomonas, Rickettsia, Rochalimaea, Salmonella, Shigella, Staphylococcus, Streptococcus, Treponema, Vibrio, Yersinia*, or a combination thereof.

In some embodiments, the one or more bacteria each independently include one or more antibiotic resistant bacteria.

In some embodiments, the one or more antibiotic resistant bacteria each independently include Methicillin-resistant *Staphylococcus aureus*, vancomycin resistant *Enterococcus*, multi-drug-resistant *Mycobacterium tuberculosis*, or a combination thereof.

In some embodiments, the one or more viruses each independently include one or more pathogenic RNA virus, one or more pathogenic DNA virus, or a combination thereof.

In some embodiments, the one or more viruses each independently include Adenoviridae, Papillomaviridae, Parvovirdea, Herpesviridae, Poxviridae, Hepadnaviridae, Polyomaviridae, Anelloviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, Hepeviridae, Hepatitis B virus, Asfarviridae, or a combination thereof.

In some embodiments, the one or more protozoa each independently include *Acineta, Actinophrys, Actinosphaerium, Amphidinium, Amphileptus, Amphisiella, Anisonema, Anthophysis, Arcella, Blepharisma, Calocyclas, Carchesium, Centropyxis, Chilodonella, Chilomonas, Colpes, Colpoda, Cyclidium, Dictyoprora, Difflugia, Dileptus, Diophrys, Disematostoma, Diplomonada, Epistylis, Euglena, Euglypha, Euplotes, Eusyringium, Frontonia, Halteria, Heliodiscus, Heteronema, Hexastylus, Ichthyophthirius, Keronopis, Lacrymaria, Leishmania, Lembadion, Lithochytris, Litonotus, Lophospyris, Loxophyllum, Nassula, Opalina, Ophrydium, Oxytricha, Paramecium, Peranema, Peridinium, Phacus, Plasmodium, Pleuronema, Podocyrtis, Pyxicola, Rhabdostyla, Rhizamoeba, Spiroloculina, Spirostomum, Stichotricha, Strombidium, Stylonychia, Tetrahymena, Thuricola, Thyrsocyrtis, Trachelomonas, Tracheloraphis Trichomonas, Trypanosoma, Urocentrum, Urostyla, Vorticella, Xiphosphaera, Xiphostylus* or a combination thereof.

In some embodiments, the one or more fungi each independently include *Alternaria, Aspergillus, Blastomyces, Candida, Ceratocystis, Chrysosporium, Coccidiodes, Cryptococcus, Epidermophyton, Exophiala, Fusarium, Helminthsporium, Histoplasma, Microsporum, Paracoccidioides, Penicillium, Paecilomyces, Pityrosporum, Saccharomyces, Sporothrix, Trichophyton*, or a combination thereof.

In some embodiments, the one or more parasites each independently include one or more parasitic roundworms, one or more parasitic flatworms, or a combination thereof.

In some embodiments, the one or more parasitic roundworms include *Ascaris*.

In some embodiments, the amygdalin is formulated as a water-soluble or lipid soluble salt or conjugate.

In some embodiments, the amygdalin includes one or more pharmaceutically acceptable purified plant extracts.

In some embodiments, the cyanogenic compound is administered with one or more antiviral medicines, one or more antibiotics, one or more antiparasitic medicines, one or more anti-malaria medicines, one or more antifungal medicines, or a combination thereof.

In some embodiments, the one or more antiviral medicines each independently include acyclovir, famciclovir, valaciclovir, amantadine, oseltamivir, rimantidine, zanamivir, cidofovir, foscarnet, ganciclovir, ribavirin, penciclovir, buciclovir, acyclic guanosine derivatives, (E)-5-(2-bromovinyl)-2'-deoxyuridine, bacavir, didanosine, emtricitabine, lamivudine, stavudine, tenofovir, zalcitabine, zidovudine, delavirdine, efavirenz, etravirine, nevirapine, amprenavir, atazanavir, darunavir, fosamprenavir, indinavir, lopinavir/ritonavir, nelfinavir, ritonavir, saquinavir, tipranavir, enfuvirtide, maraviroc, raltegravir, or a combination thereof.

In some embodiments, the one or more antibiotics each independently include cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, or a combination thereof.

In some embodiments, one or more antiparasitic medicines each independently include albendazole, amphotericin B, diethylcarbamazine, eflornithine, ivermectin, mebendazole, melarsporal, metronidazole, miltefosine, niclosamide, praziquantel, pyrantel pamoate, rifampin thiabendasole, tinidazole, yinidazole, or a combination thereof.

In some embodiments, one or more anti-malaria medicines each independently include amodiaquine, artemether, artemisinin, atovaquone-proguanil, coartem, hydroxychloroquine, lumefantrine, or a combination thereof.

In some embodiments, one or more antifungal medicines each independently include Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, ciclopirox olamine, Flucytosine, Griseofulvin, Haloprogin, Polygodial, Tolnaftate, Undecylenic acid, Crystal violet, or a combination thereof.

In some embodiments, the amygdalin, solvate, or hydrate thereof is administered with dimethyl sulfoxide.

In some embodiments, the mammal is, e.g., a human, dog, cat, horse, cow, or pig.

In a still further aspect, the invention provides a method of treating a viral infectious disease by administering a pharmaceutically effective amount of amygdalin, a solvate, or a hydrate thereof, to a mammal in need thereof.

In some embodiments the one or more viruses each independently include one or more pathogenic RNA virus, one or more pathogenic DNA virus, or a combination thereof.

In some embodiments, the one or more viruses each independently include Adenoviridae, Papillomaviridae, Parvovirdea, Herpesviridae, Poxviridae, Hepadnaviridae, Polyomaviridae, Anelloviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, Hepeviridae, Hepatitis B virus, Asfarviridae, or a combination thereof.

In some embodiments, the viral infectious disease is caused by canine parvo virus, human influenza virus, human cold virus, or feline herpes virus.

In some embodiments, the amygdalin is formulated as water-soluble or lipid soluble salts or conjugates.

In some embodiments, the amygdalin comprises one or more pharmaceutically acceptable purified plant extracts.

In some embodiments, the amygladin is administered with dimethyl sulfoxide.

In some embodiments, the mammal is a human, dog, or cat.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention are apparent from the following description, and from the claims.

DESCRIPTION

It has been discovered that there is a biochemical based "immune system" or protective mechanism that exists in the animal and human body and which forms a first line of defense against microbes and parasites. This biochemical protection is created naturally by consumption of certain food and handles the majority of viral, bacteria and parasitic infections, in some cases without full activation of the innate immune system and activation of the adaptive immune system. Therefore, very little sign of disease would appear, such as, in influenza infection, fever or sweating, since there is no cytokine activation. The biochemical shield silently eliminates the virus without alerting deeper layers of immunity. It has also been discovered that this biochemical shield can be depleted and rendered non functional. This would otherwise put an extra strain on the biological immune system such that the individual would soon become exhausted, and therefore, vulnerable to frequent infections.

Some animals, including humans, can suffer from latent immunodeficiency. Latent immunodeficiency is not a result of an immune deficiency virus, and the degree of the immunodeficiency can be so severe that the animals ("patients") can have a bacterial pneumonia or an obvious infection (e.g., open pyometra, hidden liver or kidney infection). In addition, these patients often show symptoms of toxicity (including severe weakness, loss of appetite, loss of activity, and poor response to antibiotics), yet with no indication of immune-system cell activation. Since the patient's hemogram (complete blood count (CBC)) often shows no increase in white blood cell count even after one to three weeks of post-infections the infectious origin of the disease is not detected.

Application of the compositions of the invention to a human or animal patient can restore this natural protective shield before or after a microbial infection occurs and bring about a prevention or cure of an actual infection. Treatment of the conditions as described above with cyanogenic compositions can increase the patient's white blood cell count and enhance the immune response activity of the patient against various types of infections. On average, administration of the invented medicine (two doses per day of 5 mg/Kg per dose (based on patient's body weight)) for three days results in significant (50-850%) increase of one or several types of white blood cells, as well as a rapid resolution of the clinical symptoms.

It was often observed that the body temperature of the immune compromised patients starts to elevate to fever in two to four hours after the first administration of the cyanogenic compositions, with shivering that lasts one to two hours, after which the body temperature of the treated subject becomes normal or remains slightly elevated. Significant improvement (e.g., improvement of blood count by about 80%) was observed one day after the administration of the cyanogenic composition.

The cyanogenic compound is preferably obtained from plant extracts and/or pharmaceutically acceptable salt thereof, plant extract derivatives, plant extract conjugates and/or their synthetic analogs and all of their stereo isomers, including diastereomers, enantiomers and/or other natural enzyme substrates, and administered to a subject Administration can be intravenously, intramuscularly, subcutaneously, intraperitonialy, intrapleuraly, intrabrochialy, intrauterine, orally, topically, into joints, into the urinary system, into bone and into teeth, into gingival pocket, into ear, into eye, into conjunctiva, into nose and sinuses, sublingually, intrathecally, intra-arthicularly, per rectally, into cerebrospinal fluid, applying as wound dressing, by inhalation by spray or humidified air or by any other suitable administration route.

In various embodiments, the composition is formulated in the form of a pill, capsule, granule, tablet, pallet, suspension, injection, infusion, suppository, continuous delivery system, syrup, tincture, ointment, cream, eye drops, eardrops, flush, lavage, slow absorbing depot, dressing, lozenge or any pharmaceutically acceptable application or as a nutritional supplement.

The cyanogenic compositions are preferably provided in a purified form, i.e., separated from molecules with which they are naturally associated. Purified and/or isolated cyanogenic compositions are particularly useful in the methods and compositions described herein. By "purified" or "substantially purified" is meant a cyanogenic composition that is substantially free of contaminating molecules microorganisms or other macromolecules, e.g., one or more of polysaccharides, nucleic acids, proteins or essential oils, saponins, flavanoids, ephedrine, ethanol, triterpenes, tanning agents, phytosterols, alkaloids that inhibit the activity and/or stability of the cyanogenic composition. A purified preparation contains at least 75%, 85%, 95%, 97%, 99%, or 100% of the desired composition and is substantially free of other sub-cellular components such as cytoplasmic organelles.

For example, cyanogenic compositions can be provided substantially free of hydrolytic enzymes such as emulsine, amygdalin lyase, prunasine lyase, hydroxynitrile lyase, alpha and beta glycosidase, and mannosidase.

In some embodiments, the cyanogenic compositions are provided without compositions that adversely affect their effectiveness. In some embodiments the cyanogenic compositions are also provided substantially free of iron-containing organic molecules and/or vitamins.

If the cyanogenic compositions are not separated from other constituents of the extract there can be instability, undesirable and unpredictable interactions between the cyanogenic glycoside and other constituents. For example, methylcobolamin and other analogs in small doses can inhibit amygdalin's effectiveness against viruses. Lactoferrin and/or artemisinin are also preferably absent because they can inhibit the effectiveness of cyanogenic glycosides in treating a virus infection.

For the same reasons the cyanogenic compositions are preferably provided or used in the absence of organic fruits and/or vegetable juice, which can inhibit the effectiveness of the cyanogenic compositions.

With a purified cyanogenic composition it is possible to dose the medicine properly because the quantities of the cyanogenic composition in the composition are known. Before the instant invention, the effective amount of a cyanogenic composition in a plant extract was difficult or impossible to determine because additional constituents in the extract could inhibit the effectiveness of the cyanogenic composition.

Cyanogenic Compositions

Cyanogenic compositions of the invention can be prepared using modifications of methods known in the art. The source material for the extraction can be, e.g., any suitable plant and/or seed stock known to or suspected to have a cyanogenic composition. For example, suitable sources include, e.g., Vetch seed subspecies such as *Vicia angustifolia, Vicia sativa cordata* or *nigra*, germinated sorghum seed, bitter almond, seeds from a stone fruit such as Peach (*Prunus persica*)—Kernel, Plum (*Prunus* spp.)—Kernel, Cherry (*Prunus* spp.), Apricot (*Prunus armeniace*)—Kernel, Nectarine (*Prunus persica* var *nucipersica*)—Kernel.

Typically, a first step in the process is deactivation of the hydrolyzing enzymes. This can be accomplished using one of several methods, e.g., dipping the fresh plant material into boiling alcohol, boiling the fresh plant material with acetone, or freeze-drying the plant material before extraction and, when the enzyme is deactivated, milling the plant material.

A second step is to remove oil if present with petroleum ether or another non polar solvent. A third step is a further extraction. A different extraction solvent can be used if desired. Suitable solvents for the third step include, e.g., water with citric acid, hot 50-99% methanol, a hot water-ethanol mix, or hot 99% ethanol, with refluxing for 1-6 hours, with or without sonication. The optimal extraction pH is in the range of 6.5-7.5.

The fourth step is the filtration and concentration of the extract by the evaporation of the solvent under vacuum or reverse osmosis.

The fifth step is the purification step using crystallization, HPLC, and/or slow rotary counter-current chromatography (SRCCC) or a mixture of these methods. The end product is a 95-99% pure cyanogenic glycoside composition. This composition can be used as is or mixed with different excipients.

In some embodiments, the purified composition is incubated with sodium or potassium thiosufate (e.g., a 3:1 to 6:1 ratio of cyanogenic glycoside/sodium thiosufate) to form a supramolecular complex called a tecton. This renders the cyanogenic composition safe and non toxic for medicinal use. A nomenclature to refer to the cyanogenic compositions of the invention when present in a complex with sodium thiosulfate is a BIOTECTON™ shield or VIROTECTON™ shield /tectum=shield or protect in Latin for the designation of such protective molecules/ and named to reflect the mechanism of biochemical protection.

In some embodiments, the product is very stable and can be stored at room temperature for more than two years without degradation and loss of effectiveness. It is also very safe to use since it contains no free cyanide. For this reason, high therapeutic doses (e.g., 2-15 mg/kg) can be safely administered to a patient.

While not wishing to be bound by theory, it is postulated that the cyanogenic glycoside composition is ineffective against bacteria or virus when it is tested in vitro (e.g., in a Petri dish) because the hydrolyzing enzyme of the plant, which is required for cyanide liberation, has been deactivated. However, the inventive medicine is very effective and safe in vivo because specific activation of the inventive medicine occurs with the patient's immune cells only at the site of the infection. This explains the rapid cure rate and the very low toxicity, along with its wide spectrum of activity against pathogens. Moreover, it is not the pathogen or the plant's endogenous enzymes but rather the patient's inflammatory cells that activate the molecules.

A cyanogenic composition of the invention can alternatively include commercially available amygdalin, although commercially available amygdalin is not a homogenous material but is instead is a mixture of different isomers.

Suitable cyanogenic compositions include the following:

(2R)-{[6-O-(β-D-Mannopyranosyl)-β-D-glucopyranosyl]oxy}(phenyl)acetonitrile;

(2R)-{[6-O-(β-D-Glucopyranosyl)-β-D-glucopyranosyl]oxy}(phenyl)acetonitrile;

(2R)-{[6-O-(α-L-Arabinopyranosyl)-β-D-glucopyranosyl]oxy}(phenyl)acetonitrile;

(2R)-phenyl {[6-O-(β-D-xylopyranosyl)-β-D-glucopyranosyl]oxy}acetonitrile;

2-{[(2R,3R,4S,5S,6R)-4,5-dihydroxy-6-(hydroxymethyl)-3-{[(2S,3R,4R,5R,6S)-3,4,5-trihydroxy-6-methyloxan-2-yl]oxy}oxan-2-yl]oxy}-2-(4-hydroxyphenyl)acetonitrile;

(2R)-2-phenyl-2-{[(3R,4S,5S,6R)-3,4,5-trihydroxy-6-({[(2R,3R,4S,5S,6R)-3,4,5-trihydroxy-6-(hydroxymethyl)oxan-2-yl]oxy}methyl)oxan-2-yl]oxy}acetonitrile;

(2S)-2-{[(2R,3R,4S,5S,6R)-4,5-dihydroxy-6-(hydroxymethyl)-3-{[(2S,3R,4S,5S,6R)-3,4,5-trihydroxy-6-(hydroxymethyl)oxan-2-yl]oxy}oxan-2-yl]oxy}-2-phenylacetonitrile 2-phenyl-2-{[3,4,5-trihydroxy-6-({[3,4,5-trihydroxy-6-(hydroxymethyl)oxan-2-yl]oxy}methyl)oxan-2-yl]oxy}acetonitrile;

(R)-2-phenyl-2-(((2R,3R,4S,5S,6R)-3,4,5-trihydroxy-6-((((2R,3R,4S,5S,6R)-3,4,5-trihydroxy-6-(hydroxymethyl)tetrahydro-2H-pyran-2-yl)oxy)methyl)tetrahydro-2H-pyran-2-yl)oxy)acetonitrile;

2S)-2-phenyl-2-{[(2S,3S,4R,5R)-3,4,5-trihydroxy-6-({[(2R,3R,4S,5S,6R)-3,4,5-trihydroxy-6-(hydroxymethyl)

oxan-2-yl]oxy}methyl)oxan-2-yl]oxy}acetonitrile 2-phenyl-2-{[3,4,5-trihydroxy-6-({[3,4,5-trihydroxy-6-(hydroxymethyl)tetrahydro-2H-pyran-2-yl]oxy}methyl)tetrahydro-2H-pyran-2-yl]oxy}acetonitrile;

2-phenyl-2-{[(2R,3R,4S,5S,6R)-3,4,5-trihydroxy-6-({[(2R, 3R,4R,5S,6R)-3,4,5-trihydroxy-6-(hydroxymethyl)oxan-2-yl]oxy}methyl)oxan-2-yl]oxy}acetonitrile 2-phenyl-2-{[(2R,3R,4S,5S,6R)-3,4,5-trihydroxy-6-(hydroxymethyl)oxan-2-yl]oxy}acetonitrile/prulaurasin/LD prunasin The proportion of the different isomers in a cyanogenic composition can vary depending on the type of plant material that has been used to extract the cyanogenic glycoside mixture. With the exception of prunasine they all have the same molecular weight but are different stereoisomers.

A preferred cyanogenic glycoside is a BIOTECTON™ glycoside, which is formed by mixing a cyanogenic glycoside with a sulfur-containing salt (e.g., sodium thiosulfate). When these two molecules incubated together they form tectons (self assembled molecular complexes), and this complex protects the cyanogenic glycoside from enzymatic breakdown. Therefore, this complex can be used at higher concentrations without oral and injectable toxicity relative to the usable concentration of a cyanogenic glycoside alone.

While not wishing to be bound by theory, it is postulated that the mechanism involved is not only the detoxification of the cyanide by the rhodanase enzyme using the thiosulfate as the other substrate but also the complex's stability and resistance to releasing cyanide.

A purified cyanogenic composition of the invention can be applied in an injectable form when oral administration is not indicated. For example, for some diseases oral application not possible, e.g., in the case of a subject with vomiting or diarrhea common with viral disease, and which make the absorption of the medicine unpredictable. Purified cyanogenic compositions are also very stable because no enzyme is present from the plant that can degrade the cyanogenic composition. With purified cyanogenic compositions there is no interaction or nullification of effectiveness, since only the cyanogenic compositions are present.

Treatment of Chronic Infection and Inflammation

The cyanogenic compositions can be used to treat chronic infections and (including chronic, hidden infection) and associated inflammation in different organs of the body. It has been discovered that certain chronic hidden infections in the body do not induce white blood cell elevation or do not induce a sufficiently strong immune response in the mammals body to clear an infection. These hidden infections can continue in the diseased organ for a long time with some mild and often unnoticed local inflammation until the diseased organ starts to fail and the patient develops more clinical symptoms. A this point a patient may visit a doctor and the patient is diagnosed. Unfortunately, by this time the condition is advanced and the treatment insufficient. Thus, these "hidden infections" are associated with the patient's immune system's failure to recognize the infectious organism and clear the infection.

Typical of these chronic diseases are chronic prostatitis, chronic cholangiohepatitis, chronic cystitis, chronic pancreatitis, chronic bronchitis or bronchopneumonia, chronic enteritis, and chronic glomerulonephritis. These diseases are progressive in nature, likely to recur, and often show a poor response to therapy. It has been discovered that when cyanogenic compositions are applied to patients with these chronic diseases, and a blood test is retaken 2-4 days following initiation of treatment, the previously normal white blood cell count suddenly is significantly elevated. This event is associated with clinical improvement and fast resolution of the disease. Although the mechanism not fully understood it seems that the association of the cyanogenic composition with infection improves the immune system's ability to recognize specific antigens and respond with a defense sufficiently strong to overcome the infection. The examples below show successful treatment of chronic prostatitis, chronic bronchitis or bronchopneumonia, in a dog or human using a cyanogenic composition.

Methods recited herein may be carried out in any order of the recited events that is logically possible in addition to the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, Webster's Third New International Dictionary, Merriam-Webster Inc., Springfield, M A, 1993 and The American Heritage Dictionary of the English Language, Houghton Mifflin, Boston Mass., 1981.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "adjuvant" refers to an agent that may affect any of (1) the rate of release of the drug; (2) the stability of the drug; (3) the solubility of the drug; or (4) physicochemical characteristics of the core itself, including compactness, pH, etc. However, an adjuvant does not include those ingredients that affect the release rate by providing an osmotic pressure or ion gradient. In one aspect, adjuvants may include solubilizing agents, solubility decreasing agents, and dispersing agents.

As used herein, the term "administration" of a device refers to a method of placing a device to a desired site. The placing of a device can be by any pharmaceutically accepted means such as by swallowing, retaining it within the mouth until the drug has been dispensed, placing it within the buccal cavity, inserting, implanting, attaching, etc.

These and other methods of administration are known in the art. As used herein, the term "active pharmaceutical ingredient," or API, refers to a molecular entity adapted for treatment of a malcondition in a patient in need thereof.

As used herein, the term "antibiotic" refers to a chemotherapeutic agent that inhibits or abolishes the growth of micro-organisms, for example, bacteria, fungi, or protozoa.

As used herein, the term "binder" refers to a pharmacologically inert substance, which is suitable for human consumption and serves to hold the constituents of a tablet together after compression forming of the tablet has occurred.

As used herein, the term "cancer" refers to any malignancy, solid tumor, metastasizing neoplasm, or other condition wherein cell division is uncontrolled and cells lose differentiation.

As used herein, the term "coating" refers to partial coating and adhesion or adsorption in addition to coating the whole surface of an object (e.g., core) which is to be coated. As used herein, the phrase "cyanogenic compounds, as disclosed herein" refers to the cyanogenic compounds, and pharmaceutically acceptable enantiomers, diastereomers, and salts thereof. Similarly, references to intermediates are meant to embrace their salts where the context so permits.

As used herein, the term "continuous delivery" as used herein (e.g., in the context of "continuous delivery of a substance to a tissue") is meant to refer to movement of drug to a delivery site, e.g., into a tissue in a fashion that provides for delivery of a desired amount of substance into the tissue over a selected period of time, where about the same quantity of drug is received by the patient each minute during the selected period of time.

As used herein, the term "controlled release" as used herein (e.g., in the context of "controlled drug release") is meant to encompass release of substance at a selected or otherwise controllable rate, interval, and/or amount, which is not substantially influenced by the environment of use. "Controlled release" thus encompasses, but is not necessarily limited to, substantially continuous delivery, and patterned delivery (e.g., intermittent delivery over a period of time that is interrupted by regular or irregular time intervals).

As used herein, the term "controlled drug delivery device" refers to any device wherein the release (e.g., rate, timing of release) of a drug or other desired substance contained therein is controlled by or determined by the device itself and not substantially influenced by the environment of use, or releasing at a rate that is reproducible within the environment of use.

As used herein, the term "controlled release formulation" is a formulation of a therapeutic agent wherein the release of the agent into the living body tissue of a patient is intended or designed to take place over a period of time.

As used herein, the term "delivery" refers to the release of a drug from a device comprising that drug into an environment surrounding the device. The environment into which the drug so released may or may not be the ultimate site of activity for that drug. In some instances, the released drug may need to be transported to its ultimate site of activity.

As used herein, the term "derivative" of a compound refers to a chemically modified compound wherein the chemical modification takes place at one or more functional groups of the compound and/or on an aromatic, a 5' alicyclic, or heterocyclic structures, when present. The derivative however is expected to retain the pharmacological activity of the compound from which it is derived.

As used herein, the term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the active pharmaceutical ingredient (API).

As used herein, the term "disintegrant" refers to substance that assists in dissolution of the dosage form after oral ingestion. It is believed to assist in hydration and to avoid the formation of gels in the stomach of the patient as the tablet dissolves, thus assisting in the release of the API into the gastric juices so that it can be absorbed into the bloodstream.

As used herein, the term "dispersing agent" refers to an agent that facilitates the formation of a dispersion of one or more internal phases in a continuous phase.

Examples of such dispersions include suspensions and emulsions, wherein the continuous phase may be water, for example, and the internal phase is a solid or a water-immiscible liquid, respectively. Thus, dispersing agents may include suspending agents and emulsifying agents.

As used herein, the term "dosage form" refers to a physical and chemical composition of the API that is adapted for administration to a patient in need thereof. The inventive dosage form is a tablet. By a tablet is meant a relatively hard, compact object, suitable for oral ingestion, prepared by compression of a powder including an active pharmaceutical ingredient and, usually, excipients.

As used herein, the term "dosing event" refers to administration of an agent to a patient in need thereof, which event may encompass one or more releases of an antiviral agent from a drug dispensing device. Thus, the term "dosing event," as used herein, includes, but is not limited to, installation of a continuous delivery device (e.g., a pump or other controlled release injectible system); and a single subcutaneous injection followed by installation of a continuous delivery system.

As used herein, the term "drug" refers to a therapeutic agent or a diagnostic agent and includes any substance, other than food, used in the prevention, diagnosis, alleviation, treatment, or cure of a disease. Stedman's Medical Dictionary, 25th Edition (1990). The drug can include any substance disclosed in at least one of: The Merck Index, 13th Edition, 1998, published by Merck & Co., Rahway, N.J.; Pei-Show Juo, Concise Dictionary of Biomedicine and Molecular Biology, (1996); U.S. Pharmacopeia Dictionary, 2000 Edition; and Physician's Desk Reference, 2001 Edition.

As used herein, the term "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

As used herein, the term "effective coating thickness" refers to a one-half the peak shift, where each of the central modes of the size distributions (ignoring the satellite peaks) is fit with a Gaussian.

As used herein, the term "filler" refers to a particulate material (e.g., an inorganic oxide) in dry powder form capable of being dispersed in a resin.

As used herein, the term "glidant" refers to a substance that assists in maintaining favorable powder flow properties of the powder materials that are compressed to form the inventive tablet.

As used herein, the term "hydrate" refers to the complex where the solvent molecule is water.

As used herein, the terms "include," "for example," "such as," and the like are used illustratively and are not intended to limit the present invention.

As used herein, the terms "individual," "host," "subject," and "patient" are used interchangeably, and refer to a mammal, including, but not limited to, primates, including simians and humans.

As used herein, the term "infection" refers to the invasion of the host by germs that reproduce and multiply, causing disease by local cell injury, release of poisons, or germ-antibody reaction in the cells. The infection can be in a mammal (e.g., human, dog, or cat).

As used herein, the term "vertebrate" refers to any of a subphylum (Vertebrata) of chordates possessing a spinal column that includes the mammals, birds, reptiles, amphibians, and fish.

As used herein, the term "mammal" refers to any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, such as horses, cattle, sheep, and goats, and research and domestic species, including dogs, cats, mice, rats, guinea pigs, and rabbits.

As used herein, the term "microbe" refers to an organism that is too small to be seen by the naked human eye. As used herein, the term "microbe" refers to a bacterium, a fungus, an archaea, or a protist.

As used herein, the terms "optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

As used herein, the term "patient" refers to a warm-blooded animal, and preferably a mammal, for example, a cat, dog, horse, cow, pig, mouse, rat, or primate, including a human.

As used herein, the term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications such as The United States Pharmacoepia describe the analytical criteria to assess the pharmaceutical acceptability of numerous ingredients of interest.

As used herein, the term "pharmaceutically acceptable salts" refers to ionic compounds, wherein a parent non-ionic compound is modified by making acid or base salts thereof. Examples of pharmaceutically acceptable salts include, mineral or organic acid salts of basic residues such as amines; alkali or organic salts of acidic residues such as carboxylic acids; and the like. The pharmaceutically acceptable salts include conventional non-toxic salts and quaternary ammonium salts of the parent compound formed, for example, from non-toxic inorganic or organic acids.

Non-toxic salts can include those derived from inorganic acids such as hydrochloric, hydrobromic, hydroiodic, sulfuric, sulfamic, phosphoric, nitric and the like. Salts prepared from organic acids can include those such as acetic, 2-acetoxybenzoic, ascorbic, benzenesulfonic, benzoic, citric, ethanesulfonic, e 5 thane disulfonic, formic, fumaric, gentisinic, glucaronic, gluconic, glutamic, glycolic, hydroxymaleic, isethionic, isonicotinic, lactic, maleic, malic, mesylate or methanesulfonic, oxalic, pamoic (1,1'-methylene-bis-(2-hydroxy-3-naphthoate)), pantothenic, phenylacetic, propionic, salicylic, sulfanilic, toluenesulfonic, stearic, succinic, tartaric, bitartaric, and the like.

Certain compounds can form pharmaceutically acceptable salts with various amino acids. For a review on pharmaceutically acceptable salts, see, e.g., Berge et al., *J Pharm. Sci.* 1977, 66(1), 1-19, which is incorporated herein by reference.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of many suitable salts are found in Remington: The Science and Practice of Pharmacy, 21st edition, Lippincott, Williams & Wilkins, (2005).

As used herein, the term "pharmacologically active agent" refers to a chemical compound, complex or composition that exhibits a desirable effect in the biological context, i.e., when administered to a subject. The term includes pharmacologically active, pharmaceutically acceptable derivatives of those active agents specifically mentioned herein, including, but not limited to, salts, esters, amides, prodrugs, active metabolites, isomers, analogs, crystalline forms, hydrates, and the like.

As used herein, the terms "prevent", "preventative", "prevention", "protect", and "protection" refer to medical procedures that keep the malcondition from occurring in the first place. The terms mean that there is no or a lessened development of disease or disorder where none had previously occurred, or no further disorder or disease development if there had already been development of the disorder or disease. As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "protective agent" refers to any agent which serves to prevent the occurrence of damage to an organism, such as by preventing the establishment of an infection by a microorganism, to prevent the establishment of a malcondition, to preserve an otherwise healthy body in the state of health.

As used herein, the term "solvate" refers to a complex of variable stoichiometry formed by a solute (in this invention, a cyanogenic compound, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid.

As used herein, the term "therapeutic agent" refers to any agent, which serves to repair damage to a living organism to heal the organism, to cure a malcondition, to combat an infection by a microorganism or a virus, to assist the body of the living mammal to return to a healthy state.

As used herein, the term "therapeutic composition" refers to an admixture with an organic or inorganic carrier or excipient, and can be compounded, for example, with the usual non-toxic, pharmaceutically acceptable carriers for tablets, pellets, capsules, suppositories, solutions, emulsions, suspensions, or other form suitable for use.

As used herein, the term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example by Chou and Talalay, Adv. Enzyme Regul., 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, the terms "therapy," and "therapeutic" refer to either "treatment" or "prevention," thus, agents that either treat damage or prevent damage are "therapeutic".

As used herein, the term "tissue" refers to the material forming the solid or semi-solid structures that make up any of the organs or components of a living organism, preferably human. Thus, liquids such as blood are not "tissue" according to the definition used herein, but the term "tissue" encompasses membranes, skin, muscles, bones, cartilage, nerves and nerve sheathes, meninges, connective tissue, blood vessels, the sclera or iris of the eye, the solid materials constituting internal organs such as liver, stomach, pancreas, intestine, kidney, thymus, uterus, testes, bladder, lung, heart and any other internal structures that are solid or semi-solid in texture.

As used herein, the term "topically" refers to application of the compositions of the present invention to the surface of the skin and mucosal cells and tissues (e.g., alveolar, buccal, lingual, sublingual, masticatory, or nasal mucosa, and other tissues and cells which line hollow organs or body cavities).

As used herein, the term "topically active agents" refers to compositions of the present invention that are applied to skin or mucosal surfaces. Desired pharmacological results are intended at or near the site of application (contact) to a subject.

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease.

As used herein, the term "treatment," covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used herein, "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar, and "nm" denotes nanometer.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible subranges as well as individual numerical values within that range. For example, description of a range such as 1% to 8% should be considered to have specifically disclosed subranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

Pharmaceutical Formulations

The cyanogenic compounds, as disclosed herein, are formulated with conventional carriers and excipients, which should be selected in accord with ordinary practice. Tablets typically contain excipients, glidants, fillers, binders and the like. Aqueous formulations are prepared in sterile form, and when intended for delivery by other than oral administration generally should be isotonic. All formulations optionally contain excipients such as those set forth in the Handbook of Pharmaceutical Excipients, 5th Ed.; Rowe, Sheskey, and Owen, Eds.; American Pharmacists Association; Pharmaceutical Press: Washington, D C, 2006. Excipients include ascorbic acid and other antioxidants, chelating agents such as EDTA, carbohydrates such as dextrin, hydroxyalkylcellulose, hydroxyalkylmethylcellulose, stearic acid and the like.

The pH of the formulations ranges from about 3 to about 11, but is ordinarily about 7 to 10. While it is possible for the active ingredients to be administered alone it may be preferable to present them as pharmaceutical 5 formulations. The formulations, for human use, of the cyanogenic compounds, as disclosed herein, include at least one active ingredient, as above defined, together with one or more acceptable carriers therefor and optionally other therapeutic ingredients. The carrier(s) should be "acceptable" in the sense of being compatible with the other ingredients of the formulation and physiologically innocuous to the recipient thereof. The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences, Mack Publishing Company, Easton, Pa., (1985). Such methods include the step of bringing into association the active ingredient with the carrier which constitutes one or more accessory ingredients. In general the formulations are prepared by uniformly and intimately bringing into association the active ingredient with liquid carriers, finely divided solid carriers, or both, and then, if necessary, shaping the product. Formulations of the presently disclosed subject matter suitable for oral administration may be presented as discrete units such as capsules, cachets, or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary, or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. For administration to the eye or other external tissues e.g., mouth and skin, the formulations are preferably applied as a topical ointment or cream containing the active ingredient(s) in an amount of, f 5 or example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this disclosed subject matter may be constituted from known ingredients in a known manner. While the phase may include merely an emulsifier (otherwise known as an emulgent), it desirably includes a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsif[iota]er(s) with or without stabilizer(s) make up the so-called emulsifying wax, and the wax together with the oil and fat make up the so-called emulsifying ointment base that forms the oily dispersed phase of the cream formulations.

Emulgents and emulsion stabilizers suitable for use in the formulation of the cyanogenic compounds, as disclosed herein, include TWEEN 60, SPAN 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations include one or more cyanogenic compounds together with one or more pharmaceutically acceptable carriers or excipients and optionally other therapeutic agents. Pharmaceutical formulations containing the active ingredient may be in any form suitable for the intended method of administration.

When used for oral use for example, tablets, troches, lozenges, aqueous or oil suspensions, dispersible powders or granules, emulsions, hard or soft capsules, syrups or elixirs may be prepared.

Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be used.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin, or olive oil.

Aqueous suspensions of the cyanogenic compounds, as disclosed herein, contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin. Oil suspensions may be formulated by suspending the active ingredient in a vegetable oil, such as arachis oil, olive oil, sesame oil, or coconut oil, or in a mineral oil such as liquid paraffin. The oral suspensions may contain a thickening agent, such as beeswax, hard paraffin, or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the cyanogenic compounds, as disclosed herein, are suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the cyanogenic compounds, as disclosed herein, may also be in the form of oil-in-water emulsions. The oily phase may be a vegetable oil, such as olive oil or arachis oil, a mineral oil, such as liquid paraffin, or a mixture of these.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin, or olive oil.

Aqueous suspensions of the cyanogenic compounds, as disclosed herein, contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin. Oil suspensions may be formulated by suspending the active ingredient in a vegetable oil, such as arachis oil, olive oil, sesame oil, or coconut oil, or in a mineral oil such as liquid paraffin. The oral suspensions may contain a thickening agent, such as beeswax, hard paraffin, or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the cyanogenic compounds, as disclosed herein, are suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example, sweetening, flavoring and coloring agents, may also be present.

The pharmaceutical compositions of the cyanogenic compounds, as disclosed herein, may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol, or sucrose. Such formulations may also contain a demulcent, a preservative, a flavoring or a coloring agent.

The pharmaceutical compositions of the cyanogenic compounds, as disclosed herein, may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder.

Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. The amount of active ingredient that may be combined with the carrier material to produce a single dosage form should vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight).

The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of, e.g., 0.5 to 20%, 0.5 to 10%, 1.5 to 8%, w/w.

Formulations suitable for topical administration in the mouth include lozenges including the active ingredient in a flavored basis, typically sucrose and acacia or tragacanth; pastilles including the active ingredient in an inert basis such as gelatin and glycerin, or sucrose and acacia; and mouthwashes including the active ingredient in a suitable liquid carrier.

Formulations for rectal administration may be presented as a suppository with a suitable base including for example cocoa butter or a salicylate. Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of a given condition. Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are optionally presented in unit-dose or multi-dose containers, for example sealed ampoules and vials, and may be stored in a freeze-dried (lyophilized) condition requiring the addition of the sterile liquid carrier, for example, water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In addition to the ingredients particularly mentioned above the formulations of the cyanogenic compounds, as disclosed herein, may include other agents conventional in the art having regard to the type of formulation in question, for example those suitable for oral administration may include flavoring agents.

The cyanogenic compounds, as disclosed herein, can also be formulated to provide controlled release of the active ingredient to allow less frequent dosing or to improve the pharmacokinetic or toxicity profile of the active ingredient. Accordingly, the cyanogenic compounds, as disclosed herein, also provided compositions including one or more cyanogenic compounds formulated for sustained or controlled release.

An effective dose of active ingredient depends at least on the nature of the condition being treated, toxicity, whether the compound is being used prophylactically (typically lower doses), the method of delivery, and the pharmaceutical formulation, and is determined by the clinician using conventional dose escalation studies. It can be expected to be from about 0.0001 to about 100 mg/kg body weight per day, typically, from about 0.01 to about 10 mg/kg body weight per day, more typically, from about 0.01 to about 5 mg/kg body weight per day, and more typically, from about 0.05 to about 0.5 mg/kg body weight per day. For example, the daily candidate dose for an adult human of approximately 70 kg body weight should range from 1 mg to 1000 mg, preferably between 5 mg and 500 mg, and may take the form of single or multiple doses.

If desired, the compounds of the presently disclosed subject matter may be applied in conjunction with one or more inert or inactive ingredients. The cyanogenic compounds, as disclosed herein, are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It should be appreciated that the preferred route may vary with for example the condition of the recipient.

An advantage of some of the cyanogenic compounds, a disclosed herein, is that they are orally bioavailable and can be dosed orally.

The cyanogenic compounds, as disclosed herein, can also be used in combination with other active ingredients. Such combinations are selected based on the condition to be treated, cross-reactivities of ingredients and pharmaco-properties of the combination. It is also possible to combine a cyanogenic compound, as described herein, with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect," i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills, or capsules, or by different injections in separate syringes. In general, during alternation therapy, an effective dosage of each active ingredient is administered sequentially, i.e., serially, whereas in combination therapy, effective dosages of two or more active ingredients are administered together.

Pharmaceutical kits useful in the presently disclosed subject matter, which include a therapeutically effective amount of a pharmaceutical composition that includes a compound of component (a) and one or more compounds of component (b), in one or more sterile containers, are also within the ambit of the presently disclosed subject matter. Sterilization of the container may be carried out using conventional sterilization methodology well known to those skilled in the art. Component (a) and component (b) may be in the same sterile container or in separate sterile containers. The sterile containers or materials may include separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as should be readily apparent to those skilled in the art. Instructions, either as inserts or as labels, indicating quantities of the components to be administered, guidelines for administration, and/or guidelines for mixing the components, may also be included in the kit.

In some embodiments, the cyanogenic compound is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

The cyanogenic compound can be administered 5 times per day, 4 times per day, tid, bid, qd, qod, biw, tiw, qw, qow, three times per month, or once monthly. In other embodiments, the cyanogenic compound is administered as a continuous infusion. In many embodiments, a cyanogenic compound, as described herein, is administered orally.

In connection with the above-described methods for the treatment of disease in a patient, a cyanogenic compound as described herein may be administered to the patient at a dosage from about 0.001 mg to about 100 mg/kg patient bodyweight per day, in 1 to 5 divided doses per day. In some embodiments, the cyanogenic compound is administered at a dosage of about 5 µg to about 50 mg/kg patient bodyweight per day, in 1 to 5 divided doses per day.

The amount of active ingredient that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill should readily appreciate that dose levels can vary as a function of the one or more cyanogenic compounds, the severity of the symptoms and the susceptibility of the subject to side effects. Preferred dosages for a given cyanogenic compound are readily determinable by those of skill in the art by a variety of means. In many embodiments, multiple doses of one or more cyanogenic compounds are administered. For example, a cyanogenic compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

It is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

The invention will be further illustrated in the following non-limiting examples.

Example 1. Preparation and Testing of a BIOTECTON™ Cyanogenic Composition

A BIOTECTON™ glycoside contains 400-500 mg mandelonitrile glycosides and about 100 mg sodium thiosulfate in water solution. These are incubated in a water bath 30-50° C. for 1-3 hours. During this time color changes occur with some recrystallization and dissolution, but after several hours the no additional color change occurs. When this process occurs at room temperature it takes about 24 hours to complete the complex formation.

This complex has no toxic effect at a dose of 5000 mg/body weight kg by oral application while the literature has LD50 for amygdalin about 900 mg/body weight kg. The BIOTECTON™ glycoside has about 20-30% longer effectiveness than previously described amygdalin isomers.

To demonstrate the effectiveness of a BIOTECTON™ glycoside composition, a double-blind pasteurella infection test was performed on rabbits in the Pharmacology and Toxicology Department of the Veterinary University of Hungary. In the infected control group, 100% of the rabbits died while all (100%) of the rabbits treated with the BIOTECTON™ glycoside composition survived. Moreover, pasteurella could not be cultured out of the live rabbits.

Example 2. Treatment of Canine Parvovirus Infections Using a Cyanogenic Composition Canine parvovirus gastro enteritis on young unvaccinated dogs typically exhibits a mortality rate of approximately 85%. Dogs that survive recover within seven days. With aggressive support therapy the mortality rate drops to about 20-40%, depending upon the virulence of the strain.

35 dogs aged 2-4 months of mixed gender and breed and suffering from canine parvoviral infections and testing positive with the SNAP Parvo Elisa Test were subcutaneously injected once with a lactated ringer solution calculated on about a 6 weight percent (wt %) dehydration rate. The dogs were injected subcutaneously twice a day for five days with about a 10 mg/kg dose of the aqueous solution of cyanogenic composition sodium amygdale prepared as described herein.

Typically, vomiting and diarrhea had subsided significantly on all dogs within 24 hours of the beginning of the treatment. After 48 hours, only two dogs had weak diarrhea. After 72 hours, all dogs were diarrhea free. No adverse effects were observed during or after this treatment regime. All of the dogs completely recovered with the five day treatment regime.

Eleven of the thirty five dogs were in extreme duress at the beginning of the treatment and probably would have died without the treatment. The final analysis of the data reveals about a 60-80% faster recovery time, the complete elimination of any mortality, and a 60-95% reduction of symptoms after the first injection.

Example 3. Treatment of Human Cold and Flu Infections Using a Cyanogenic Composition A 53-year 82 kg man typically exhibited the following symptoms during the course of a flu infection: (1) inflammation of the nasopharyngeal membrane on Day 1; (2) inflammation of the throat mucosa membrane and a cough, sore throat, runny nose, as well as nasal congestion on Day 2; and (3) severe tracheitis. When left untreated, general symptoms generally included, for example, fatigue, loss of appetite, muscle ache, joint ache, and sweating that appeared on Day 1, increased through Day 3, and persisted for 8-14 days.

During his next infection, the same 53-year 82 kg man exhibited: (1) inflammation of the nasopharyngeal membrane on Day 1; (2) inflammation of the throat mucosa membrane and a cough, sore throat, runny nose, nasal congestion on Day 2; and (3) severe tracheitis. Treatment was begun on Day 1 by orally administering a total dose of about 200 mg of a cyanogenic composition prepared as described herein twice per day (about 5 mg/kg bodyweight per day) for the first two days, then a dose of about 100 mg of amygdalin twice per day (about 2.5 mg/kg bodyweight per day) for the next two days. After the first day, all flu symptoms disappeared.

Example 4. Treatment of Feline Rhinotracheitis Using a Cyanogenic Composition Seventeen cats ages two months to three years suffering from feline rhinotracheitis with symptoms of fever, loss of appetite, coughing, sneezing, nasal discharge, conjunctivitis, and pneumonia were divided into Groups A and Group B.

The Group A cats (8 cats total) were given the oral antibiotic clavomox at a dosage of about 10 mg/kg of bodyweight 5 twice a day. These cats did not improve until after 6 or 7 days. Three cats continued to show symptoms of nasal discharge for up to two weeks.

The Group B cats (9 cats total) were subcutaneously injected with about a 10 mg/kg dose of the aqueous solution of a cyanogenic composition prepared as described herein at a dosage of about 10 mg/kg bodyweight once per day for three days. After three days, all clinical symptoms had disappeared.

Example 5. Preliminary Toxicology Studies of a Cyanogenic Composition

A preliminary toxicology study was conducted on five white mice. An acute toxicology dose of a cyanogenic compound prepared as described herein was applied up to 5000 mg/body Kg/day. Separate oral and injection trials were conducted. No toxicity event was detected after five consecutive days of application. All five mice survived at least one month after termination of the study.

The in-vitro test also showed that even in high concentration a cyanogenic composition was not toxic to the cells in cell culture. While not wishing to be bound by theory, it is postulated that the low toxicity of the cyanogenic composition is the result of a unique molecular complex formation. This complex is responsible for the resistance of the molecule against hydrolysis, even in the presence of a hydroxynitrile lyase. The molecular complex forms on the acetonitrile moiety of the cyanogenic glycosides in the presence of the sodium thiosulfate and water during incubation. In a water solution the acetonitrile portion accepts a proton and becomes positively charged. The thiosulfate ion is negatively charged and at the double bond on the sulfur side the ion is hydrophobic, and therefore no water shell covering can occur. The thiosulfate ion coordinates with the protonated positively charged acetonitrile. This complex formation interferes with the lyase enzyme activity on the molecule and blocks hydrogen cyanide formation, hence the very low toxicity.

The protonation on the acetonitrile side of the water solution is made possible by the higher proton affinity of acetonitrile compared to water. $H_2O$ proton affinity 166.5 (kcal mol-1), CH3CN proton affinity 188.0 kcal mol-1).

A further in vivo acute toxicity study was performed in 18 mice using oral or intraperitoneal administration. The study was conducted in three dose groups—three mice in each—for both oral and intraperitoneal administration, respectively.

For animal welfare reasons a starting dose of 300 mg/kg body weight (cf. OECD 423, Annex 2 c: Starting dose is: 300 mg/kg bw.) was chosen. Animals received 300, 2000 and 5000 mg test substance BIOTECTON®" cyanogenic composition for one kilogram of bodyweight in a single oral or intraperitoneal dose. Gross pathology and histopathology tests were performed two weeks post-treatment.

The BIOTECTON® cyanogenic test composition was a clear, transparent, and sterile solution. Purity data and description of physico-chemical properties were not available. The test substance vehicle was a sterile physiological (0.9% w/v) saline solution. This vehicle is an isotonic and isosmotic solvent frequently applied in injection liquids as a carrier (cf. USP, PhEUR).

White laboratory mice of the BDF1-strain were used in the study. The test animals were bred and kept using routine procedures, according to their microbiological status. In this test 18 adult, male mice were used. Their age was between 10 and 12 weeks at the start of the trial.

The test animals were obtained from the National Institute of Oncology (Budapest, Hungary). The mice were kept in standard rodent boxes (40×12.5×12 cm), three animals per allocation. The room temperature was between 21-23° C. The relative air humidity was between 50-65% RH during the study. The feeding was managed from trough feeders, with watering from bottles. An artificial light program was applied with 12 hour light and 12 hour dark periods.

The animals were randomly selected, marked to permit individual identification, and kept in their cages for seven days prior to dosing to allow for acclimatization to laboratory conditions. In this trial a sterile watery solution of a BIOTECTON® cyanogenic composition was administered to laboratory mice.

The animals received a single oral or intraperitoneal dose of the test substance, respectively. The application was performed based on the instructions of the OECD 423 guideline. Treatments were performed with either the diluted (with physiological, sterile saline) or non-diluted (100 and 200 mg/ml) formulation of BIOTECTON® cyanogenic compositions.

The test substance in the PO group was administered in a single dose by gavage using a stomach tube, and administered to the IP group in a single dose using sterile disposable plastic syringe and needle (G25). Three animals per route of application were used for each step. First, mice were treated two times three (per oral and intraperitoneal) animals received 300 mg/kg bw. of the test BIOTECTON® substance. No mice died.

The test was then continued with the administration of 2000 mg/kg in next 3 plus 3 animals, respectively. Because of the absence of lethal effect in 2000 mg/kg groups, another 3 plus 3 mice were treated orally or intraperitoneally with 5000 mg/kg dose after another four hours observation.

The test mice received standard rodent feed and water in drinking quality ad libitum during the whole trial. The animals were fasted on the day of the administration of the test substance. Feeding was withheld for 4 hours prior the application. Mice received their next feeding two hours after the receiving the drug.

Animals were observed individually after dosing once during the first 30 minutes and then periodically during the first 24 hours, with special attention given during the first 4 hours, and daily thereafter, for a total of 14 days. The following table (Table 2) shows the results of clinical observation. Observations included changes in skin and fur, eyes and mucous membranes, and also respiratory, circulatory, autonomic and central nervous systems, and somatomotor activity and behaviour pattern.

No evidence of any clinical sign of toxic reaction was detected in low or in high doses the PO or IP treated groups of mice.

Individual weights of animals at the day of dosing, in weekly intervals thereafter, and at time of death or sacrifice were recorded.

Prior to the scheduled sacrifice not a single animal died. In the time course of post treatment period no sign of toxic reaction was observed. Each animal remained healthy and survived the two weeks of the post-treatment observation period.

All test animals participated in the trial survived, and at the end of a two week observation period they were subjected to gross necropsy. Animals were euthanized by cervical dislocation. Gross pathology examination and the weights of the liver, spleen, and right kidney were recorded individually.

Liver, spleen, kidney, lung, heart, and small intestine tissue samples were subjected to histopathological examination. In 11 mice of 18 fatty infiltration of the liver was detected, presumably reflecting good body condition. The minor alterations in internal organs detected with histopathology are vital reactions, and cannot be considered as the consequence of supposed toxic effect of test substance. In six animals (No 1, 4, 7, 12, 16, 18) the liver was hyperaemic, and the lung tissue was hyperaemic only in animal No 7. In spleen tissue, lymphoid depletion was observed in animals 6 and 7. In the same tissue the signs of megacytosis were detected in one PO and three IP treated animals. However, these alterations do not appear to be in strong positive correlation with the applied dose. In animal No 5 slight segmental tubular nephrosis was seen (possibly due to another harming effect). Fusion of the intestinal villi occurred in 8 animals of 18, but possibly not as the result of the administration of test substance.

Acute oral toxicity refers to those adverse effects occurring following oral administration of a single dose of a substance, or multiple doses given within 24 hours. Delayed death means that an animal does not die or appear moribund within 48 hours but dies later during the 14-day observation period (OECD 423).

The mice showed neither weight loss, other adverse effects nor delayed death following administration of the BIOTECTON® cyanogenic composition. Although histopathology examination revealed light signs of splenotoxicity (i.e. megacytosis) and some other minor alteration of internal organs were observed in several treated animals, the absence of clinical signs and lethality shows the BIOTECTON® cyanogenic composition can be considered as a practically non toxic agent according to both per os (PO) and intraperitoneal (IP) application. After the single application of 5000 mg/kg BIOTECTON®, as the upper limitation on testing (OECD 423), neither clinical sign of toxicity nor lethal effect could be detected. BIOTECTON® can thus be considered as a practically harmless substance, regarding to the Globally Harmonised Classification System for Chemical Substances (GHS).

Example 6. In Vitro Efficacy of a Cyanogenic Composition Against Canine Parvovirus 2 (CPV2)

Without wishing to be bound by theory, it is postulated that the compositions of the invention are pro-drugs and as such become activated after entering a patient's body. The activation takes place at the site of the infection in the tissue or blood by the innate immune system where ever inflammation occurs in the patient. These types of medicines cannot be tested with the traditionally conducted in-vitro test for efficacy evaluations. Instead, the composition was tested and compared in a canine parvovirus cell culture system and in live dogs.

Method and Materials:

The virus was cultured in 25 $cm^2$ flask. Each flask contained 250000 MDCK cells and was infected with 109 TCID50 type two dog parvovirus (canine parvovirus 2, CPV2) in the University of Veterinary Science Hungary department of Virology. Each test was repeated three times. A BIOTECTON cyanogenic composition prepared as described herein in a CPV2 viral culture:

1. Flask: 10 ml growth medium, 0 mg/ml Biotecton /1. Positive control/
2. Flask: 10 ml growth medium, 0 mg/ml Biotecton /2. Positive control/
3. Flask: 10 ml growth medium, 0 mg/ml Biotecton /3. Positive control/
4. Flask: 10 ml growth medium, 20 mg/ml Biotecton
5. Flask: 10 ml growth medium, 20 mg/ml Biotecton
6. Flask: 10 ml growth medium, 20 mg/ml Biotecton
7. Flask: 10 ml growth medium, 200 mg/ml Biotecton
8. Flask: 10 ml growth medium, 200 mg/ml Biotecton
9. Flask: 10 ml growth medium, 200 mg/ml Biotecton
10. Flask: 10 ml growth medium, 400 mg/ml Biotecton
11. Flask: 10 ml growth medium, 400 mg/ml Biotecton
12. Flask: 10 ml growth medium, 400 mg/ml Biotecton
13. Flask: 10 ml growth medium, negative control /NO CPCV2 infection of cells/

The flasks were incubated for five days. After incubation the flasks were cooled to −20° C. to freeze the culture. The freeze-thaw cycle was repeated three times to free the viruses from the cells. 100 ml of liquid from each flask was next boiled for 10 minutes, then placed on ice for 5 minutes. The freed CPV2 nucleic acid was determined three times using real-time PCR. The results are presented below.

| Sample: Flask number real-time PCR | Cycle threshold by experiments | Average Cycle threshold By flask | Cycle threshold Biotecton concentration average |
|---|---|---|---|
| 1/1 | 20.72 | 21.35 | 0 mg/ml Biotecton |
| 1/2 | 20.85 | | 19.15 |
| 1/3 | 22.50 | | |
| 2/1 | 18.22 | 17.40 | |
| 2/2 | 18.52 | | |
| 2/3 | 15.47 | | |
| 3/1 | 20.00 | 18.71 | |
| 3/2 | 19.71 | | |
| 3/3 | 16.42 | | |
| 4/1 | 20.47 | 20.37 | 20 mg/ml Biotecton |
| 4/2 | 20.14 | | 19.17 |
| 4/3 | 20.49 | | |
| 5/1 | 19.18 | 18.21 | |
| 5/2 | 19.96 | | |
| 5/3 | 15.50 | | |
| 6/1 | 18.41 | 18.98 | |
| 6/2 | 19.84 | | |
| 6/3 | 18.67 | | |
| 7/1 | 18.18 | 18.20 | 200 mg/ml Biotecton |
| 7/2 | 18.32 | | 17.4 |
| 7/3 | 18.10 | | |
| 8/1 | 16.45 | 17.44 | |
| 8/2 | 18.43 | | |
| 8/3 | 17.44 | | |
| 9/1 | 16.90 | 16.56 | |
| 9/2 | 16.40 | | |
| 9/3 | 16.37 | | |
| 10/1 | 17.55 | 17.76 | 400 mg/ml Biotecton |
| 10/2 | 17.04 | | 17.38 |
| 10/3 | 18.68 | | |
| 11/1 | 18.71 | 17.90 | |

-continued

| Sample:<br>Flask number real-<br>time PCR | Cycle<br>threshold by<br>experiments | Average<br>Cycle<br>threshold<br>By flask | Cycle threshold<br>Biotecton concentration<br>average |
|---|---|---|---|
| 11/2 | 17.35 | | |
| 11/3 | 17.63 | | |
| 12/1 | 16.75 | 16.94 | |
| 12/2 | 16.36 | | |
| 12/3 | 17.71 | | |

The cycle threshold is that point where the double strand DNA production during PCR first can be measured. A lower level of cycle threshold is indicative of a higher amount of DNA in the sample, which indicates virus production.

The test results show that up to 20 mg/ml Biotecton concentration in the growth media did not reduce cycle threshold, indicating no in-vitro blocking of virus propagation. Very high concentration of Biotecton incre stomatitis. The recovery time varied between 1 day and 6 days. The average recovery time was 4 days.

Recovery was determined by a person with no knowledge of the treatment groups and who only evaluated the presence or absence symptoms.

Norovirus gastroenteritis is very similar to FCV and treatment efficacy. Thus, putative norbirus therapies are often tested using the feline virus. To date no resistance against the inventive treatment has been detected on any bacterial, viral, or protozoa disease that has been treated. Treatment of humans and animals has been conducted in clinical settings for a total period of four years in two different countries and in many different clinics. Many routine cases were treated successfully and with a 100% repeatability that was documented but is not listed below. The examples are not anecdotal in nature but rather conducted against the currently available medical standard treatment as control. Current medical studies of effective treatments merely compare the efficacy of a treatment with a placebo. The inventive medicament and treatment was primarily aimed against diseases that have no currently good effective treatment.

Example 9. Treatment of Bacterial Lung Infection in a Cat Using a Cyanogenic Composition The effectivness of a cyanogenic composition was tested on a 16 year old cat diagnosed with very severe bacterial pneumonia. The cat was not eating, was recumbent, coughing and dyspneic, with symptoms increasingly worsening for two weeks prior to treatment with the cyanogenic composition. The cat had been previously been treated with amoxicillin, which resulted in a slight improvement followed by a relapse.

The cat was admitted to an animal hospital and treated for seven days with 10 mg/body weight Kg/day with the cyanogenic composition. At the end of the treatment the cat was eating well, active, walking fine. There has not been any relapse.

Example 10. Treatment of Protozoan Parasitic Infestation in a Dog

An eight week old female immune compromised Chihuahua /runt of the litter was am emergency admission to an animal hospital. The dog was not able to walk and was in lateral recumbence. Clinical symptoms included frequent vomiting and diarrhea. A diagnostic fecal test identified a severe *Giardia* infection. Giardiasis is a protozoan parasites that typically lasts 2-4 weeks and can be resistive to treatment.

The puppy was treated with 5 mg/Kg/day injection of the cyanogenic composition and some supportive therapy. In five days she completely recovered and her *Giardia* infection on a follow-up fecal test was confirmed negative. The puppy was eating, playful and very active by the fifth day.

Example 11. Treatment of a Severe Idiopathic Neurological Syndrome in a Dog

A one and a half year old Chihuahua with severe neurological symptoms was presented in the hospital for treatment. The clinical signs were anisochoria /unequal pupils/, head tilt, proprioceptive deficit, and seizure. The owner refused a diagnostic workup but insisted on treatment. The clinical signs indicated brain pathology and the relatively slow development that lasted two weeks prior to treatment and the gradually increasing severity of seizure and other symptoms and the age of the dog indicated infectious or parasitic origin rather than traumatic.

The dog was treated with 10 mg/kg/day of the cyanogenic composition in one dose subcutaneous injection/day for 6 days in the hospital. At the end of the 6th day of treatment the dog was completely cured. The seizure, the head tilt the anisochoria and the proprioceptive deficit symptoms disappeared. The dog was happy, active and eating well, and was released from the hospital. A two week follow up confirmed the complete recovery with no reoccurrence.

Example 12. Treatment of Combined Viral, Bacterial, and Parasitic Invention in a Dog Resistant to Other Treatment Protocols with a Cyanogenic Composition A six mouth old Shih Tzu presented at an animal clinic with very severe cough, vomiting, diarrhea and severe lethargy. The dog was previously diagnosed in another hospital with heavy infection of Kennel cough, *Giardia* and *Isospora* infections. Treatment was started with Azithromycin and Clavamox at therapeutic dose sin another hospital about 2 weeks previously, but the symptoms did not abate. The medication was switched to Enrofloxacin and Clavomox was continued. However, the symptoms continued to worsen to the point where the dog was so weak it could not stand.

Kennel cough infection is a combination infection of Parainfulenza virus and *Bordetella bronchiseptica* bacteria. In this young dog a concurrent infection of bacteria, virus and 2 parasites was present and proved to be resistant to treatment with antibiotics but the inventive treatment cured the dog quickly.

The dog was then treated with 10 mg/kg/day inj. of a cyanogenic composition prepared as described herein. The dog recovered quickly and completely in five days.

Example 13. Topical Treatment of a Bacterial Ear Infection Using a Cyanogenic Composition for a Bacterial Ear Infection A five year old dog presented with a yellow left ear and a pussy, smelly discharge. The ear was painful on exam with lot of puss in the ear canal. Aerobic ear culture was negative for Coagulase and negative *Staphylococcus* and Beta Hemolytic *Streptococcus*.

The treatment consisted of a topical application pr 3-5 drops (about 12 cc) of 75 mg/ml water based of the cyanogenic composition applied twice daily. The solution was dispensed in a home treatment.

A follow up revealed complete healing with no recurrence. The smelly, painful, and pussy discharge resolved within five days, although the treatment continued for ten days in a form of topical ear drops and no other medication.

Example 14. Preventing Disease Development in a Unvaccinated Two Month Old Dog that Had Tested Positive with ELISA Parvo Virus Antigen Test Using a Cyanogenic Composition A two month old pit bull puppy with an appointment for its first shots was suspected to have a medical condition because the dog's medical history revealed two days of being lethargic anorexic, and its mother had not had vaccines. A parvovirus Elisa test was performed and was positive. The dog had not yet developed the typical clinical symptoms of vomiting and diarrhea because of the very early detection of the virus. Suspecting that the condition would worsen, the poppy was hospitalized and received 10 mg/kg cyanogenic composition twice/day /75 mg BID/ for 5 days.

No vomiting developed, and the dog had one incidence of mild diarrhea on the second day. After the second day its appetite and general condition returned to normal. After five days of treatment the dog was released from the hospital and continues to be healthy. On follow up no symptoms of parvovirus gastro enteritis had developed.

Without treatment, parvoinfection in eight weeks or younger unvaccinated puppies born in a litter to an unvaccinated mother has 100% morbidity and close to 100% mortality with severe clinical symptoms of diarrhea, vomiting, anorexia with very fast progression to death. The fact that the puppy did not develop the disease other than a single incident of diarrhea in the second day, even though he was Elisa fecal test positive, shows the effectiveness of the cyanogenic composition treatment as a preventative medicine.

Example 15. Treatment of a Bacterial Bone Infection in a Canine Mouth Using a Cyanogenic Composition A 13 year old mixed breed, 24 lb dog with halitosis and mouth bleeding and black stools from swallowing blood was presented to an animal hospital. Oral exam revealed severe periodontal disease of the right upper canine teeth a bone infection with fistula and bleeding gum on the roof of the mouth.

Dental work was scheduled, and an injection of the cyanogenic composition was given at 10 mg/kg dose. The dog went home with 5 tab of 100 mg/tab once a day. No other medication was given. The dog returned for dental cleaning and extraction 4 days later. Under anesthesia the oral exam revealed a complete healing of the previously bleeding gum and the fistula. The complete healing occurred only in 4 days—the infection had been cleared out of the bone.

Example 16. Treatment of a Therapy Resistant Respiratory Infection in a Cat Using a Cyanogenic Composition A two year old domestic short hair cat, six pounds, body weight, temp 102° F. emaciated cat came from a cat holding facility and was FIV and FELV negative. Its clinical symptoms: very severe wheezing respiration, very moist cough, frequent sneezing all day beginning 10 days previously. The cat had been treated in another hospital previously with antibiotics: first, clavamox oral /contains amoxicillin and with β-lactamase-inhibiting effect clavulanic acid known as for powerful, broad-spectrum antimicrobial activity. Five days later treatment was continued with convenia injections, long acting broad spectrum fourth group cephalosporin, but the condition continued to worsen. CBC chemistry blood work was performed. The only abnormality was a 40% increase in Monocytes above the highest normal, and mild anemia.

A cyanogenic composition was then injected into the cat at 33 mg/kg one time and continued with 30 mg tablet/day SID orally, which represents 11 mg/body weight Kg for nine consecutive days. Two days later the cat was reported to be doing much better, with no more sneezing. Treatment with the cyanogenic composition worked instantly, according to the owner, while treatment with the antibiotic therapy did not.

Ten days later a follow up examination and vaccination was performed. The cat remained healthy, had gained weight, was eating well, and wheezing, coughing, and sneezing was absent.

Example 17. Treatment of Severe Acute Parvo Virus Gastro-Enteritis in a 4 Month Old Unvaccinated Dog Using a Cyanogenic Composition A 4 month old 9.9 lb male dachshund presented to an animal hospital with vomiting and a history of bloody diarrhea for three days. The frequency of the vomiting was 12 times/day and diarrhea 2 times/day. An examination reviled lethargy, muscular weakness, and 6% dehydration. Abdominal palpation indicated significant amounts of fluid in the intestine. A parvo fecal antigen test was strongly positive. The puppy was hospitalized and put on iv lactated ringer fluid therapy and 75 mg of a cyanogenic composition twice/day IM injections /represents 16.8 mg/kg twice/day dose/. The fluid therapy and the inventive medication continued for four days.

In the first day the dog had one mucosal bloody diarrhea event. No additional events were observed throughout the therapy nor was any vomiting detected. After the third day the puppy become active and its appetite returned. After four days he was released from the hospital active and healthy. The dog remained healthy when returned one week later for recheck and vaccinations.

A fully developed parvo infection with prior art therapy takes 10-14 days of supportive therapy while the immune system copes with the viral infection. In unvaccinated dog the mortality rate is quite high. This example shows that treatment with a cyanogenic composition of the invention can reduce hospital stays more than 50% and reduce the mortality rate close to 0% with injection therapy twice/day.

Example 18. Treatment of Severe Septic Fever in a Cat with a Concurrent Maxillary Bone Infection A cat reported by its owner to be four years old presented with a weight of 13.5 lb, symptoms of anorexia, with meowing from pain, weakness, and a putrid smell from the mouth. The cat's temperature was 104.1° F. and its pulse was weak and rapid. A mouth exam revealed infection of the maxillary bone with a pussy discharge and odor due to periodontal disease. The compromised general condition indicated a handling of the septic condition before dental work with anesthesia could be administered.

The cat received one injection of the cyanogenic medicine 120 mg SC /19.75 mg/kg dose/.

The cat's temperature was periodically measured to identify the effectiveness of the treatment. The starting temp was 104.1° F. at 11 AM. At 12:30 PM the temperature dropped to 102.8° F. By 7 PM the temperature was a normal 101.1° F. The cat was more alert and responsive. Its pulse was full and at a normal rate, indicating the resolution of septicemia. Treatment was successful without any other medication or supportive therapy.

Example 19. Treatment of Bartonellosis in a Cat with a Cyanogenic Composition An eight year-old domestic short hair female cat presented with a history of not eating and not drinking for two days and lethargy. Its body weight was 10.6 lb and its temperature was 104.4 F.° (high fever). A *Bartonella henselae* test was positive. Total bilirubin 1.5 mg/dl high /normal range 0.1-0.4 mg/dl/ Neutrophiles 17112/ul high /normal range 2500-8500/ul/.

The cat was treated with one injection sc 70 mg of the cyanogenic composition. Its temperature was monitored as follows: 2 hours after injection the temperature was 104.0° F., four hours after injection the temperature was 103.4° F.; 12 hours after injection of the cyanogenic composition the temperature was 101.2° F. (normal). The cat went home from the hospital. A recheck phone call one week later revealed that the cat was eating and active. The cat continued to act normally.

In contrast to the single injection treatment of the cyanogenic composition, the standard treatment of doxycycline or amoxicillin usually requires 1-2 weeks of antibiotic treatment.

Example 20. Treatment of Upper Respiratory Infection in a Dog

A Pekingese dog 1½ years old presented weighing 13.1 lb with a temperature of 101.5° F. after coughing all day for the previous two days. The coughing began after the Pekingese had been exposed to a coughing dog.

The Pekingese dog's general condition and appetite were normal. The diagnosis: acute trachio-bronchitis due to infection.

The dog was treated with a cyanogenic composition 15 mg/kg injection sc and sent home with 25 mg tab of cyanogenic composition 12 tab. Dose was 1 tab twice/day. No additional therapy or medicine were administered. On a follow up examination one week later the owner told that the dog was much better after two days and stopped coughing completely four days after treatment with the cyanogenic composition began. Usually with conventional standard antibiotic therapy the coughing can last two-three weeks. Even with cough suppressant it is difficult to make the dog comfortable. In contrast, treatment with but with the cyanogenic composition made the dog comfortable and facilitated rapid healing.

Example 21. Treatment of a Dog Multi-Drug Resistant *Pseudomonas aeruginosa* Middle Ear Infection with a Cyanogenic Composition A six old Yorkie 13.5 lb BW presented with recurring right ear pussy discharge and bad odor coming from the right ear. The ear was very itchy and the dog was constantly scratching it. The dog had been suffering with this ear infection for about a year and a half with multiple antibiotic treatments at other veterinary clinics with only slight temporary improvement. After the therapy ended the dog had relapsed quickly.

A physical examination revealed a severe, pussy middle ear infection. The inside of the right ear had significant swelling and redness. A culture sensitivity ear swab was taken and processed by a diagnostics laboratory (Antech). The culture revealed:
Aerobic Culture and Mic from ear swab
Organism: *Pseudomonas Aeruginosa*
Heavy growth
/sensitive=S; resistant=R/
MIC ug/ml antibiotic: amikacin<=8 S, amoxicillin n/a R, ampicillin n/a R, cephadroxil n/a R, cefazolin n/a R, cefoxitin>=32 R, cefpodoxime>=8 R ceftiofur>=8 R, cephalexin n/a R, Clavamox n/a R, cefovecin>=R, enrofloxacin<=0.5 S, gentamicin<=2 S, marbofloxacin<=1 S, potentiated sulfonamide n/a R The results from the ear swab indicated that this *Pseudomonas* was resistant to ten antibiotics and sensitive only for four antibiotics. In addition, multi-resistant *Pseudomonas aeruginosa* present a therapeutic challenge because of its tendency to form biofilms that prevent even the best antibiotics from reaching the microorganism at therapeutic concentrations.

The dog was treated by applying 3-4 drps of a 6% cyanogenic composition to the right ear twice/day for 10 days and 60 mg sc injection at the time of visit followed by 20 mg twice/day of oral inventive medication for 10 days. No additional medications were used.

Follow up: One day after the start of treatment the dog significantly decreased scratching. According to owner, the dog was much better than before and resting comfortably. A recheck at 10 days after treatment revealed a significant decreased swelling of the right ear, no pussy discharge and odor, and no more scratching. Since the infection was handled the dog underwent a minor surgery.

Example 22. Treatment of Chronic Suppurative Prostatitis /Prostate Abscess in a Dog with a Cyanogenic Composition An eight year old Akita dog presented suffering from chronic, recurring prostatitis with typical clinical symptoms associated with the condition. Ultrasound exam revealed a 2×3 cm large cavity in the prostate. The dog was treated several times with different antibiotics like enrofloxacin and clavamox and showed only temporary mild improvement, followed by a quick relapse. This condition had worsened in the previous eight months, causing significant suffering by the pet and frustration to the dog's owner.

A cyanogenic composition was administered to the dog to attempt to improve the condition before attempting surgery. The dog was receiving 10 mg/bw kg injection twice/day of cyanogenic composition in the first week and showed an 80% clinical improvement. In the second week the dose was adjusted to 5 mg/kg inj. twice/day. This resulted in a complete clinical recovery. After two 2 weeks of treatment an ultrasound exam on the prostate showed that the previous prostate cavity had shrunk to 1×1 cm. The treatment continued in the 3rd week with 2 mg/bw kg dose twice/day. At the end of the third week the ultrasound exam revealed that the prostate cavity completely disappeared. The surgery was not performed since the complete recovery and cure of the condition. A recheck was performed three times over a two month period and showed no recurrence.

Example 23. Treatment of Intracellular *Rhodococcus equi* Infection in a Horse Using a Cyanogenic Composition A horse aged three months was diagnosed with Rhodococcosis following a bacterial culture. Antibiotic sensitivity testing showed erythromycin and rifampin resistance. The foal had a fever, coughing, and rapid respiration. The clinical pneumonia symptoms were progressing fast. Previous incidents of severe cases like this one showed approximately 100% mortality on this farm. Since no alternative treatment was available, treatment was attempted with a cyanogenic composition. The foal was given 5 mg/kg of a cyanogenic composition inj. twice/day for 14 days. Complete recovery was reported for the foal, and no side effects were detected during and after treatment.

Example 24. Treatment of Epstein-Barr-Virus Caused Infectious Mononucleosis in a Human Using a Cyanogenic Composition A 54-year old man tested the cyanogenic composition on himself for treating infectious mononucleosis caused by Epstein-Barr virus. He was a practicing veterinarian who was familiar with the cyanogenic compositions of the invention, had used the cyanogenic compositions to treat animals with viral diseases, and had acquired confidence in the effectiveness and safety of the treatment. He self medicated after earlier treatment he received was ineffective and even harmful.

The man's disease condition started with fever, fatigue, and swollen lymph glands in the neck. The medical diagnosis was Epstein-Barr virus caused infectious mononucleosis. Initial treatment was with a large dose of steroid /methylprednisolone/ injection, which helped to reduce the severe lymph gland swelling in the neck. However, a side effect of the steroid and the concurrent virus infection prolonged the condition with severe fatigue, with overall worsening of the general condition and severe pain. The condition within one week progressed to the point to near fainting.

The veterinarian was admitted to a hospital where the diagnosis of Epstein-Barr virus caused infectious mononucleosis was confirmed and he was given a prognosis of 2-3 mouth of debilitating fatigue and slow recovery. The veterinarian started administering a cyanogenic composition to himself at home after he was released after 4 days of hospitalization, during which time he had not improved. The dose used for self medication was 200 mg 3×/day. The veterinarian fully recovered in seven days and did not relapse in more than one year. No side effects were detected following the therapy with the cyanogenic composition.

Example 25. Treatment of Human Respiratory Viral Infection Treatment During Three Years of Flu Seasons with a Cyanogenic Composition Cyanogenic compositions were orally administered to a human with a common cold and flu. The treatment was taking place over three flu seasons on a 54 years old male with 82 kg of bodyweight and no known medical condition other than frequent bouts of flu in winter.

Medical history revealed a total tonsillectomy /pharyngeal and nasal/ at age of 8 and frequent common cold or flu episodes (about 5-6) every winter. The frequency and severity of symptoms had increased in the past 10 years. The severity and extent of the symptoms was somewhat stronger then the typical cold due to the lack of upper respiratory protective lymphatic ring and the presence of two school age children in the household who brought home from school new virus strains.

Symptoms and progression and duration of the disease had not varied too much over the past 10 years except for a slight increase in severity. Symptoms followed a typical progression from the onset of the infection to recovery regardless of the treatment.

A flu shot administered to revent the frequent flu instead caused severe flu symptoms comparable to natural infection and with no significant decrease of frequency or severity of subsequent flu in that season.

The course of infection episode started with inflammation of nasopharyngeal mucosal membrane the 1st Day, continuing with inflammation of the throat and larynx mucosal membrane. Day 2 showed cough, sore throat, runny nose, and nasal congestion. During days 2-3 a severe tracheitis was present. The patient described this symptoms by saying "It feels like my trachea was burned with a hot iron rod." General symptoms, such as fatigue, loss of appetite, muscle and joint ache, sweating, increased from the first day to the 3 day significantly and remained with the other cold symptoms for 8-14 days. This patient over the past 10 years had tried every available medical and other alternative treatments to shorten or alleviate the disease with no apparent benefit.

The cyanogenic composition was used to treat every episode of cold and flu disease on this patient over three flu seasons, totaling about 16 treatment regimens. The treatment started at the first day of onset of inflammation of the nasopharyngeal mucosal membrane. The total dose administered was 200 mg 2 times per day /about 5 mg/kg bodyweight per day/ for the first 2-4 days and continued with total dose 100 mg 2 times per day /2.5 mg/kg bodyweight per day/ for 2-4 days. This regiment was used in each application to prevent development of flu symptoms. No other treatment was applied.

The treatment resulted in complete prevention of flu symptoms. No cold or flu symptoms have appeared in this patient for three flu seasons when treatment was started at the early sign of the disease. Every treatment completely eliminated the disease from the first day and prevented its progression. The only symptoms detected were tiredness for 1-2 days, but the symptoms did not prevent the patient from working. No adverse reaction was detected during any of the 16 treatment regimens. No adverse reaction occurred during and after treatments.

The patient allowed the flu to progress on four different occasions to a full development of the disease as it described above. On the 3rd and 4th day, when the flu symptoms fully developed the cyanogenic composition was applied. For the first 2 days the dose of medicine was 200 mg 3×/day, the 3-5 days 200 mg 2×/day and 6-7 days 100 mg 2×/day was applied. The flu symptoms completely resolved in 1-3 days after the initiation of treatment without any other medication.

The grading of the clinical symptoms, like quantification of sneezing time, nasal discharge, or grading of the general condition is very difficult after administering the cyanogenic composition since the improvement is very rapid. In some cases I has taken only 2-3 hours it take to resolve 90% of the existing clinical symptoms. Thus, there have been no symptoms to tabulate. The therapy time generally needed to continue for about seven days. In the case of early termination of therapy, the flu symptoms tend to come back 2-3 days following the last treatment.

The common cold and flu is caused by viral infection of the respiratory tract and can be caused by more than 200 different type of viruses. The most common viruses involved in the disease are rhinoviruses but also common are human Para influenza viruses, adenoviruses, picornaviruses, corona viruses, human respiratory syncytial viruses, metapneumoviruses, influenza A or B or C viruses. The current scientific literature agrees that there are no medications or herbal remedies that have been conclusively demonstrated to shorten the duration of infection. The reason for this failure to cure the disease lies in the multiplicity of causes and often mixed infection of different viruses at the same time. Usually, viral medications only treat only certain viruses and are ineffective for other types. The current inventive medications are not specific to a certain virus but are effective against very broad spectrum of viruses. Thus, any of the causative agents of the disease can be successfully treated.

Example 26. Treatment of Human Respiratory Viral Infection Treatment in Eight Adult Volunteers Using a Cyanogenic Composition The inventive medication was taken orally by eight adult volunteers, mixed gender, between 22-75 years of age, in Budapest, Hungary. The treatment protocol was 3-5 mg/kg body weight 2 times/day for 7 days. The treatment was started 1-2 days after the onset of flu symptoms. The result was a complete recovery within 1-2 days depending on the severity of symptoms at the time of the beginning of the inventive treatment. No side effects associated with the treatment were reported. The eight volunteers requested additional cyanogenic compositions because of its effectiveness they experienced with the treatment.

Example 27. Treatment of a Reccurring *Candida albicans* Vaginal Yeast Infection with a Cyanogenic Composition A 35 year-old volunteer woman 57 kg body weight with frequent recurring vaginal *Candida albicans* infection was diagnosed and treated by her gynecologist over a period of 15 years. The reccurrence frequency was 2-3 flare ups every year for the past 15 years. The gynecologist first administered lotrimazole (brand name CANESTEN™ oral capsule and cream) for 5-7 days with a good symptomatic response. However, 3-6 months later the infection would again appear. Chlorhexidine wash was also tried to prevent recurrence to no effect.

In the absence of an effective therapy to prevent the flare up the volunteer applied a cyanogenic composition at a dose of 200 mg twice/day orally for 5 days with a complete resolution of the clinical symptoms. No flare-up has been detected for at least three years. No other treatment was used since there had been no recurrence.

Example 28. Treatment of *Herpes simplex labialis* Using a Cyanogenic Composition A 38 year-old volunteer woman, 54 kg suffered from recurring herpes outbreaks on the lip since aged 18 years. The outbreaks happened about every two years and were associated with immune compromised conditions like stress, concurrent upper respiratory infection and menstrual cycles. The outbreaks last approximately 7-9 days and no spontaneous remission of an outbreak had occurred.

The outbreaks always followed a predictable progression and included a tingling sensation, redness and swelling of about 5 mm area on upper right side middle of the lip and 2-4 days after the onset blisters appear that turns into a scab that last about 5 days. The only medicine that could slightly alter this course was Zovirax crema /acyclovir/ if the treatment began at the first sign of an outbreak. No other medicine had any effect on alleviating symptoms. With the treatment of Zovirax the blister size smaller (about 4 mm in diameter) and the duration of the outbreak was shorter (to approximately 5 days).

The cyanogenic composition was used to see if it could obtain better results treating a new outbreak. Topical and oral cyanogenic composition medications were applied simultaneously with no other medication. The topical medicine included 6% concentration cyanogenic composition in neutral ointment base 3×/day applied to the outbreak site on the lips and the oral cyanogenic composition was taken in a dose of 200 mg as one time dose.

The result of the treatment: resolution of all symptoms and no progression of the herpes infection in 2 days and no latent flare up after the treatment stopped.

Example 29. Treatment of Canine Neurological Distemper Infection with a Cyanogenic Composition Two dogs presented with neurological distemper infection //paramyxovirus/ meningeoencephalitis. The two were treated at separate times but are presented together since they had nearly identical histories.

The dogs were 8-10 months old and adopted from a shelter and had no vaccination history. A medical history revealed a mild respiratory disease 3-4 week prior to the symptoms of developing temporal muscle twitching, leg muscular twitching, hypersensitivity to touch and noise, and short 15-20 second seizures once or twice a day. The symptoms developed over a week with increasing intensity. Distemper titer IgG and IgM were highly positive. The absence of a recent vaccination resulted in a diagnosis of neurological canine distemper.

The cyanogenic composition was administered at a dose of 15 mg/BW kg injection twice/day for the first week and 15 mg/Bw kg once a day for the second week. This treatment completely resolved the clinical symptoms in one dog and about 80% of the symptoms in the other dog. The only remaining symptom was a slight twitching of leg and shoulder muscles in one dog. However, the dog was able to walk normally after treatment while walked with difficulty prior to the treatment.

The causative agent of distemper I is very similar nature to human measles virus infection /virologically and clinically. This suggests that the cyanogenic compositions can be useful in treating human measles, which can cause encephalitis in children and adults with high mortality.

Example 30. Treatment of *Malassezia pachydermatis* Otitis in Dogs Using a Cyanogenic Composition A five year old cocker spaniel was diagnosed with a *Malassezia pachydermatis* ear infection based on a stained slide microscopic exam and s physical exam. The dog had a recurring ear infection with substantial itching and brown wax production, as well as a strong smell and redness in both ears.

The dog was treated using a cyanogenic composition. The treatment consisted of 3-5 drops of a 5% aqueous solution of the cyanogenic composition placed in each ear twice/day. The treatment was continued for 2 weeks.

The clinical symptoms of itching redness of the ear subsided significantly by the 3 day of treatment and all clinical symptoms resolved by day 6 of the therapy. A two month recheck confirmed the lasting effect of the therapy.

Example 31. Treatment of *Trichophyton* Infection of the Feet in Human /Athletes' Foot/ Using a Cyanogenic Composition A volunteer young swimmer volunteer with a severe itchy, scaly fungal infection on the feet was presented for treatment. The infection was most severe between the toes with some fissure and red and inflamed skin. The treatment included 7% of a cyanogenic composition in neutral ointment base with DMSO. Approximately 30 minutes after the first treatment the itching completely stopped. The treatment continued twice/day for five days in which time the scaling, redness and itching completely resolved. No side effects were observed during and after the treatment.

Example 32. Treatment of a Dog with Chronic Hepatitis, Pancreatitis and Acute Hemorrhagic Gastroenteritis Using a Cyanogenic Composition A common denominator in successfully treated cases discussed in these examples is inflammation in the body. Inflammation in the body is caused by the innate immune system as a response to invading microorganisms. Inflammation is not a specific reaction to a specific microorganism but rather a general and uniform response of the animal and human body when challenged by pathogenic agents like bacteria, viruses, fungi, parasites, and protozoa. A cyanogenic composition contacting the inflamed area in or on the body gets enzymatically activated and turns into a therapeutic agent locally by releasing cyanide in a discrete amount that kills the pathogen. While not wishing to be bound by theory it is postulated that this is the reason for the wide spectrum and uniform workability regardless of the genus of the pathogens and this is the reason for the extreme low toxicity.

To elucidate the toxicity limits of the cyanogenic composition, it was compared with known substances.

Table salt LD 50 /Lethal dose on 50% of recipients/ 3000 mg/kg caffeine LD 50 150-200 mg/kg aspirin LD50 200-1200 mg/kg A cyanogenic composition was tested orally and by injection at a dose 5000 mg/kg body weight. No clinical sign of toxicity was detected. Therefore, the composition was considered as GRAS /generally regarded as safe/ tested on mice.

The animals also tested on autopsy and histological studies were made of liver, kidney, brain, muscle, and pancreatic tissue. These organs did not show any pathological change microscopically or macroscopically after the animals received a large dose of the cyanogenic composition.

Example 33. Treatment of Chronic Cholangiohepatitis in a Cat Using a Cyanogenic Composition A cat with chronic cholangiohepatitis presented with jaundice, had stopped eating, and was very lethargic. Blood work showed elevated levels of liver enzymes but no elevation of white blood cell levels.

A cyanogenic composition treatment regimen was initiated. After 2-3 days of 3× treatment at 10 mg/kg BID plus force feeding and fluid therapy the white blood cell count increased significantly (to about 20-24 thousand). The cat started to eat by itself, the cat's activity improved. The jaundice subsided and the other symptoms resolved. The treatment continued for 4-6 days. No treatment failures were reported, in contrast to standard antibiotic therapy.

Example 34. Treatment of a Dog with Inflammatory Bowel Disease (IBD) and Chronic Enteritis with a Cyanogenic Composition A dog presented with symptoms of chronic weight loss during the previous three months. Watery diarrhea 3-6 times/day was the main complaint and clinical symptom. The dog was treated with a cyanogenic composition 5 mg/kg twice/day for 10 days. The diarrhea stopped and the dog gained weight.

Example 35. Treatment of a Cat with Chronic Glomerulonephritis with a Cyanogenic Composition Chronic glomerulonephritis is a common disease in older cats. Symptoms include anorexia, anemia, weight loss, frequent urinating, and thirst. Blood work reveals a BUN /blood urea nitrogen/ 80-180, creatinine 4-7, phosphorous is often elevated and no elevation in white blood cell count.

A cat with symptoms of chronic glomerulonephritis was treated with a cyanogenic composition iv or sc inj. 10 mg/kg dose BID for 2-5 days. This treatment usually increases the white blood cell count /mainly neutrophyls/ to 18-22 thousand. Treatment with the cyanogenic composition reduced the BUN level about twice as quickly as did fluid therapy and antibiotic therapy alone. The cats treated with the cyanogenic composition started to eat after two days and were sent home after 3-5 days of treatment. A follow-up check revealed the BUN level significantly improved to about 30-50 depending on the initial level.

Example 36. A Cyanogenic Glycoside Composition-Thiosulfate Supramolecular Complex is Resistant to Bacterial Enzyme Hydrolysis/Degradation and Liberation of Toxic Cyanide The use of sodium thiosulfate application to treat victims of cyanide exposure and the attendant cyanide toxicity is well known in the medical field. Large volumes of sodium thiosulfate intravenous injection in a dose of 250 mg/body weight kg are administered to a patient suffering from clinical cyanide toxicity. The mechanism involved in the endogenous cyanide detoxification is a enzymatic transsulfuration by a rhodanese enzyme to thiocyanate, which is relatively non toxic.

The cyanogenic compositions of the invention, in contrast, avoid liberating free cyanide with its subsequent detoxification. Cyanogenic glycosides break down and liberate cyanide when mixed with a bacterial beta glycosidase enzyme to become toxic. Intestinal bacteria, for instance, can produce a beta glycosidase enzyme cause free cyanide development or, in a strong bacterial infection like septicemia, cyanide liberation can occur inside the patient's body. In fact, a lethal dose of 50% of recipient /LD 50/ of oral amygdalin is 400-900 mg/kg. according to scientific literature.

In contrast, supramolecular complex formation of cyanogenic glycoside compounds with sodium thiosulfate according to the invention avoids this potential toxicosis. This was illustrated in a controlled toxicology study where 5000 mg/kg caused no toxic events in mice following either oral administration or injection.

Supramolecular complex formation was tested by the new complex's ability to resist enzymatic degradation and subsequent cyanide liberation in-vitro by bacterial enzymes.

An in vitro test was performed to differentiate this extreme low toxicity from a detoxification mechanism in the body versus from no cyanide liberation.

The test was performed on:
1. A non complexed cyanogenic glycoside and
2. A thiosulfate-complexed cyanogenic glycoside in separate test tube incubated with mixture of standardized intestinal bacteria culture Free cyanide formation was measured.

Test Method:

First test: three separate test tubes were set up each with: 5 ml of cyanogenic glycoside /200 mg/ 5 ml concentration/ was incubated with 13 billion live bacterial culture for 12 hours in a temperature of 35 C. After 12 hours the mix was centrifuged and the top aliquot was tested for free cyanide concentration.

Second test: Three separate test tubes were set up each with: 5 ml of sodium thiosulfate incubated with a cyanogenic glycoside complex. The concentration of the cyanogenic glycoside was 100 mg/ml and the concentration of the sodium thiosulfate was 25 mg/ml. The cyanogenic glycoside and sodium thiosulfate were mixed and incubated at 40° C. for 12 hours before using it in the test. This incubation period was enough time for the supramolecular complex to form. From this solution 2 cc was mixed with 3 cc sterile water and was incubated with 13 billion live bacteria for 12 hours in a temperature of 35° C. After 12 hours the mix was centrifuged and the top aliquot was tested for free cyanide.

Bacterial culture contains 13 billion live bacteria such as: *L. rhamnosus, L. casei, L. acidophilus, L. plantarum, L. bulgaricus, L. salivarius, E. faecium, S. thermophilus, B. longum, B. breve.*

Cyanide testing was performed with a colorimetric test with the sensitivity of 0.01-0.20 mg/Liter free cyanide with the increments of −0.00, −0.01, −0.02, −0.03, −0.05, −0.07, −0.10, −0.12, −0.15, −0.20.

Result:

First test free cyanide: −0.10, −0.12, −0.10; Second test free cyanide: −0.00, −0.00, −0.00.

Conclusion:

The complexed cyanogenic glycoside did not liberate cyanide, while the natural cyanogenic glycoside released free cyanide after 12 hours of incubation with bacteria. This indicates that the supramolecular complex provides stability to the complex in the presence of hydrolyzing enzyme and interferes with the bacterial enzyme's ability to breakdown down the molecule. Therefore, the very low toxicity results from the prevention of cyanide liberation rather than from detoxification.

Example 37. Treatment of Open Pyometra in a Dog Using a Cyanogenic Composition An eight year old female pit bull, 50.3 Lb dog with subnormal body temperature (98.7 F (ref. range: 101-102.5 F)) was presented in the animal hospital. The dog had shown severe lethargy and lack of energy for one week, had lost appetite and weight, and had been drinking an excessive amount of water for two weeks. Pus was observed in the vaginal area of dog, and an X-ray examination revealed a moderately enlarged uterus.

Complete blood count (CBC) of the dog (by Antech Diagnostics (accession No. NYAC49153631)) showed a low white blood cell count (2.4 thousand/μL (ref. range: 4.0-15.5 thousand/uL), including neutrophils: 1440/μL (ref. range: 2060-10600/μL), bands 0/μL (ref range: 0-300/μL), lymphocytes: 192/uL (ref. range: 690-4500/μL), monocytes: 768/μL (ref. range: 0-840/μL), eosinophils 0/uL (ref. range: 0-1200/μL), and basophils 0/μL (ref. range: 0-150/μL)). This blood wok analysis demonstrated a total lock of immune response or an exhausted immune system, indicating a clinically severe bacterial infection. The diagnosis of the dog's symptoms was open pyometra.

The dog was then treated with a cyanogenic composition (5 mg/Kg per dose (based on the dog's body weight), two doses per day. After three days of administration of the invented medicine, the total white blood cell count of the dog significantly increased by 6.75 times (16.2 thousand/pt, including neutrophils: 11178/μL, lymphocytes: 3564/μL, monocytes: 1134/μL, Bands: 0/μL, eosinophils: 324/μL, and basophils: 0/μL). The elevated level of white blood cell count was also accompanied by a significant clinical improvement. The body temperature of the dog was increased to a normal level, and increased activity and appetite of the dog were observed. The dog was then strong enough to go under an ovary-hysterectomy surgery.

Example 38. Treatment of Chronic Suppurative and Eosinophilic Bronchopneumonia in a Dog Using a Cyanogenic Composition An eight year old male Dachshund, 29.3 lb dog exhibited chronic respiratory conditions including coughing, severe lethargy, fever (103.8 F), crackles sound over both sides of lungs, and no heart murmurs was presented in the animal hospital.

The dog was initially treated with (Clavomox tabs, 125 mg per tab, 1.5 tab per dose, two doses per day). After ten days of administration of the described medicine, the dog showed no clinical improvement. Radiography examination of the dog revealed lung infiltration, and the attending veterinarian next prescribed Cephalexin (250 mg per tab, one tab per dose, one dose per day for 10 days).

After five weeks, the dog was returned to the hospital with a severe coughing with bloody phlegm in sputum, and X-ray examination showed bronchiectasis and chronic bronchopneumonia with 60% lung involvement. Tracheal wash, wash cytology and culture sensitivity test were performed to the dog. The wash cytology showed a suppurative and eosinophilic inflammation, and the culture sensitivity test identified a multiresistant *pseudomonas aeruginosa* with resistance to most antibiotic including Cephalexin and Clavamox, which have been used previously dog and showed no success due to the resistance. The culture sensitivity test also identified an oral antibiotic Marbofloxacin being sensitive.

Surprising and unusual test results were also found in the complete blood count of the dog. Despite the chronic aggressive bacterial suppurative infection, no increase in white blood cell count suggesting immune response was observed (6 thousand/uL (ref range: 4-15.5 thousand/uL), including neutrophils: 3360/μL (ref. range: 2060-10600/μL), bands: 0/μL (ref. range: 0-150/μL), lymphocytes: 1620/μL (ref. range: 690-4500/μL), monocytes: 300/μL (ref. range: 0-840/uL), eosinophils: 720/μL (ref. range 0-1200/μL), and basophils: 0/μL (ref. range 0-1504/μL)).

The dog was then treated with a cyanogenic composition (5 mg/kg twice a day. After three days of the treatment with the invented medicine, the clinical symptoms of the dog were significantly improved. The dog showed less coughing and showed increased activity. A CBC test indicated an elevated monocyte count (984/μl) and eosinophil count (1804/μl), indicating the cyanogenic composition activates an immune response along with bringing about clinical improvement.

Example 39. Treatment of Chronic Kidney Failure, Latent Immune Deficiency in a Dog Using a Cyanogenic Composition A nine year old Pomeranian dog with vomiting, painful abdomen, weakness, loss of appetite, and unsteady walking for one week was presented in the clinic. Complete blood count test of the dog reveled a significant elevation of kidney values (blood urea nitrogen: 100 mg/dL (ref. range: 6-31/dL), creatinine: 2.5 mg/dL (ref. range: 0.5-1.6 mg/dL). The CBC test also identified a low white blood cell count (1.6 thousand/μl (ref. range 4-15.5 thousand/μl), including neutrophils: 1296/μl (ref range: 2060-10600/μL), bans: 0/μL (ref range: 0-150/μL), lymphocytes: 160/μL (ref range: 690-4500/μL), monocytes: 128/μL (ref. range 0-840/μl), eosinophils: 16/μl (ref. range: 0-1200/μL), and basophils 0/μL (ref. range: 0-150/μL)), indicating a lack of immune response. The diagnosis of the dog's symptoms was concluded as kidney failure and latent immune deficiency.

The dog was then treated with a cyanogenic composition (lactated ringer IV and thiosulfate complexed cyanogenic glycoside, 5 mg/Kg per dose (based on the dog's body weight) administered once a day. After three days of administration of the invented medicine, the dog showed a 40% decrease of blood urea nitrogen (from 100 mg/dL to 62 mg/dL), and a significant increase of white blood cell count (11.0 thousand/μL, including neutrophils: 9570/μL, bands 0/μL, lymphocytes 330/μL, monocytes 1100/μL, eosinophils 0/vL, and basophils 0/μL). Significant clinical improvements such as a returned appetite were also observed after three days, and with a returned strength the dog was released healthy on the fifth day.

Conclusion:

The complexed cyanogenic glycoside did not liberate cyanide, while the natural cyanogenic glycoside released free cyanide after 12 hours of incubation with bacteria.

It is to be understood that the foregoing description is intended to illustrate and not to limit the scope of the invention, which is defined by the scope of the appended claims. Other embodiments are within the scope of the following claims.

What is claimed is:

1. A pharmaceutical composition comprising a substantially purified cyanogenic compound complexed with sodium thiosulfate; wherein the cyanogenic compound is a cyanogenic glycoside; wherein the pharmaceutical composition comprises between 0.01 mg and 30 mg of the cyanogenic glycoside per kg of body weight of the subject; and wherein the mass ratio of the cyanogenic glycoside to sodium thiosulfate is between 6:1 and 3:1.

2. The composition of claim 1, wherein the cyanogenic compound is separated from hydrolytic enzymes with which it is naturally associated, wherein the hydrolyzing enzymes include emulsine, amygdaline lyase, prunasine lyase, hydroxynitrile lyase and beta glycosidase, and mannosidase.

3. A method of treating an infectious disease in an animal in need thereof, the method comprising administering to the animal a pharmaceutically effective amount of the pharmaceutical composition of claim 1.

4. The pharmaceutical composition of claim 1, wherein the cyanogenic compound is
   (2R)-{[6-O-(β-D-Mannopyranosyl)-β-D-glucopyranosyl]oxy}-(phenyl)acetonitrile;
   (2R)-{[6-O-(β-D-Glucopyranosyl)-β-D-glucopyranosyl]oxy}-(phenyl)acetonitrile;
   (2R)-{[6-O-(α-L-arabinopyranosyl)-β-D-glucopyranosyl]oxy}-(phenyl)acetonitrile;
   (2R)-phenyl {[6-O-(β-D-xylopyranosyl)-β-D-glucopyranosyl]oxy}-acetonitrile; 2-{[(2R,3R,4S,5 S,6R)-4,5-dihydroxy-6-(hydroxymethyl)-3-{[(2S,3R,4R,5R,6 S)-3,4, 5-trihydroxy-6-methyloxan-2-yl]oxy}oxan-2-yl]oxy}-2-(4-hydroxyphenyl)acetonitrile;
   (2R)-2-phenyl-2-{[(3R,4 S,5 S,6R)-3,4, 5-trihydroxy-6-({[(2R,3R,4S,5 S,6R)-3,4,5-trihydroxy-6-(hydroxymethyl)oxan-2-yl]oxy}methyl)oxan-2-yl]oxy}acetonitrile;
   (2S)-2-{[(2R,3R,4S,5 S,6R)-4,5-dihydroxy-6-(hydroxymethyl)-3-{[(2S,3R,4S,5 S,6R)-3,4, 5-trihydroxy-6-(hydroxymethyl)oxan-2-yl]oxy}oxan-2-yl]oxy}-2-phenylacetonitrile;
   2-phenyl-2-{[3,4,5-trihydroxy-6-({[3,4, 5-trihydroxy-6-(hydroxymethyl)oxan-2-yl]oxy}methyl)oxan-2-yl]oxy}acetonitrile;
   (R)-2-phenyl-2-(((2R,3R,4S,5 S,6R)-3,4,5-trihydroxy-6-((((2R,3R,4S,5 S,6R)-3,4,5-trihydroxy-6-(hydroxymethyl)tetrahydro-2H-pyran-2-yl)oxy)methyl)tetrahydro-2H-pyran-2-yl)oxy)acetonitrile;
   (2S)-2-phenyl-2-{[(2S,3 S,4R,5R)-3,4,5-trihydroxy-6-({[(2R,3R,4S,5 S,6R)-3,4, 5-trihydroxy-6-(hydroxymethyl)oxan-2-yl]oxy}methyl)oxan-2-yl]oxy}acetonitrile;
   2-phenyl-2-{[3,4,5-trihydroxy-6-({[3,4, 5-trihydroxy-6-(hydroxymethyl)tetrahydro-2H-pyran-2-yl]oxy}methyl)tetrahydro-2H-pyran-2-yl]oxy}acetonitrile;
   2-phenyl-2-{[(2R,3R,4S,5 S,6R)-3,4, 5-trihydroxy-6-({[(2R,3R,4R,5 S,6R)-3,4,5-trihydroxy-6-(hydroxymethyl)oxan-2-yl]oxy}methyl)oxan-2-yl]oxy}acetonitrile;
   2-phenyl-2-{[(2R,3R,4 S, 5 S,6R)-3,4,5-trihydroxy-6-(hydroxymethyl)oxan-2-yl]oxy}acetonitrile.

5. The method of claim 3, wherein the infectious disease is caused by one or more of bacteria, one or more viruses, one or more protozoa, one or more fungi, one or more parasites, or a combination thereof.

6. The method of claim 5, wherein the one or more bacteria each independently comprise one or more antibiotic-resistant bacteria.

7. The method of claim 5, wherein the one or more viruses each independently comprise one or more pathogenic RNA virus, one or more pathogenic DNA virus, or a combination thereof.

8. The pharmaceutical composition of claim 1, wherein the cyanogenic compound is formulated as a water-soluble or lipid-soluble salt.

9. The pharmaceutical composition of claim 1, wherein the cyanogenic compound is present in one or more pharmaceutically acceptable purified plant extracts.

10. The method of claim 3, wherein the animal is a mammal.

11. The method of claim 10, the domesticated mammal is a horse, cow, goat, pig, dog, cat, or rabbit.

12. The method of claim 10, the mammal is a human.

13. A method of treating an inflammatory disorder in a mammal in need thereof, the method comprising administering to the mammal a pharmaceutically effective amount of the pharmaceutical composition of claim 1; wherein the inflammatory disorder is inflammatory bowel disease, stomatitis, prostatitis, hepatitis, pancreatitis, cystitis, bronchitis, kidney disease, or mastitis.

14. The pharmaceutical composition of claim 1, wherein the cyanogenic compound comprises a positively charged acetonitrile moiety that coordinates with the sodium thiosulfate to generate a molecular complex.

* * * * *